(12) United States Patent
Fahrner et al.

(10) Patent No.: US 7,485,704 B2
(45) Date of Patent: Feb. 3, 2009

(54) REDUCING PROTEIN A LEACHING DURING PROTEIN A AFFINITY CHROMATOGRAPHY

(75) Inventors: Robert L. Fahrner, San Mateo, CA (US); Amy Laverdiere, San Francisco, CA (US); Paul J. McDonald, San Francisco, CA (US); Rhona M. O'Leary, San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 257 days.

(21) Appl. No.: 10/877,532

(22) Filed: Jun. 24, 2004

(65) Prior Publication Data

US 2005/0038231 A1     Feb. 17, 2005

Related U.S. Application Data

(60) Provisional application No. 60/490,500, filed on Jul. 28, 2003.

(51) Int. Cl.
*C07K 16/00* (2006.01)
(52) U.S. Cl. .................. 530/413; 530/412; 530/387.1
(58) Field of Classification Search .................. None
See application file for complete search history.

(56) References Cited

U.S. PATENT DOCUMENTS

| 5,622,700 | A | 4/1997 | Jardieu et al. |
| 5,725,856 | A | 3/1998 | Hudziak et al. |
| 5,821,337 | A | 10/1998 | Carter et al. |
| 6,127,526 | A | 10/2000 | Blank |
| 6,333,398 | B1 | 12/2001 | Blank |
| 6,927,044 | B2 * | 8/2005 | Stahl et al. .................. 435/69.7 |

FOREIGN PATENT DOCUMENTS

| WO | 95/22389 | 8/1995 |
| WO | WO 96/30046 | 10/1996 |
| WO | WO 98/23645 | 6/1998 |
| WO | WO 98/23761 | 6/1998 |
| WO | WO 98/45331 | 10/1998 |
| WO | WO 01/00245 | 1/2001 |
| WO | WO 03/041859 | 5/2003 |
| WO | WO 2004/076485 | 9/2004 |

OTHER PUBLICATIONS

Balint et al., "Evidence for Proteolytic Cleavage of Covalently Bound Protein A from a Silica Based Extracorporeal Immunoadsorbent and Lack of Relationship to Treatment Effects" *Transfusion Science* 16:85-94 (1995).
Fahrner et al., "Expanded bed protein A affinity chromatography of a recombinant humanized monoclonal antibody: process development, operation, and comparison with a packed bed method" *Journal of Biotechnology* 75:273-280 (1999).
Gagnon, P., "Affinity Chromatography: The Fine Print" *Validated Quarterly Resource Guide for Downstream Processing* (www.validated.com/revalbio/pdffiles/affinity.pdf) pp. 1-5 (1999).
Horenstein et al., "Design and scaleup of downstream processing of monoclonal antibodies for cancer therapy: from research to clinical proof of principle" *Journal of Immunological Methods* 275:99-112 (2003).
Schuler et al., "Development and optimization of a single-step procedure using protein A affinity chromatography to isolate murine IgG monoclonal antibodies from hybridoma supernatants" *Journal of Chromatography* pp. 61-70 (1991).
Tu et al., "Temperature affects binding of murine monoclonal IgG antibodies to protein A" *Journal of Immunological Methods* 109:43-47 (1988).
van Sommeren et al., "Effects of temperature, flow rate and composition of binding buffer on adsorption of mouse monoclonal $IgG_1$ antibodies to protein A Sepharose 4 Fast Flow" *Preparative Biochemistry* 22(2):135-149 (Jun. 1992).
Carter et al., "Humanization of an Anti-p185$^{HER2}$ Antibody For Human Cancer Therapy" *Proc. Natl. Acad. Sci. USA* 89:4285-4289 (May 1992).
Kim et al., "The Vascular Endothelial Growth Factor Proteins: Identification of Biologically Relevant Regions by Neutralizing Monoclonal Antibodies" *Growth Factors* 7(1):53-64 (1992).
Presta et al., "Humanization of an Anti-Vascular Endothelial Growth Factor Monoclonal Antibody for the Therapy of Solid Tumors and Other Disorders" *Cancer Research* 57(20):4593-4599 (Oct. 15, 1997).
Werther et al., "Humanization of an Anti-Lymphocyte Function-Associated Antigen (LFA)-1 Monoclonal Antibody and Reengineering of the Humanized Antibody for Binding to Rhesus LFA-1" *J. of Immunology* 157:4986-4995 (1996).

* cited by examiner

*Primary Examiner*—Marianne P Allen
(74) *Attorney, Agent, or Firm*—Atulya R. Agarwal; Ginger R. Dreger; Goodwin Procter LLP

(57) ABSTRACT

A method for reducing leaching of protein A during protein A affinity chromatography is described which involves reducing temperature or pH of, or by adding one or more protease inhibitors to, a composition that is subjected to protein A affinity chromatography.

12 Claims, 6 Drawing Sheets

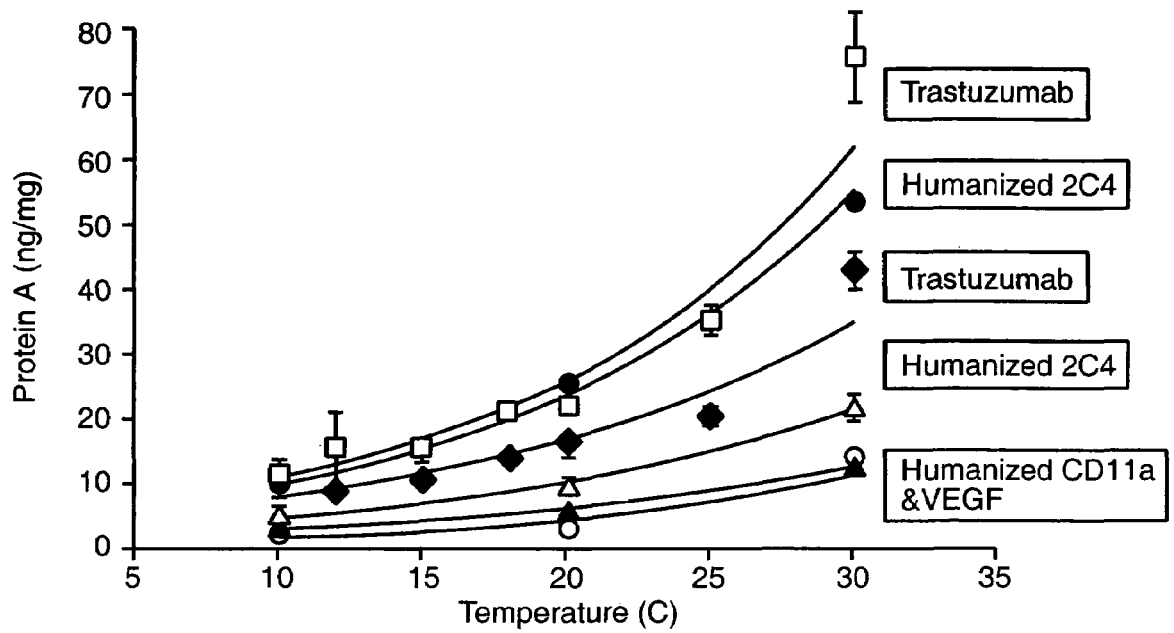
FIG._1
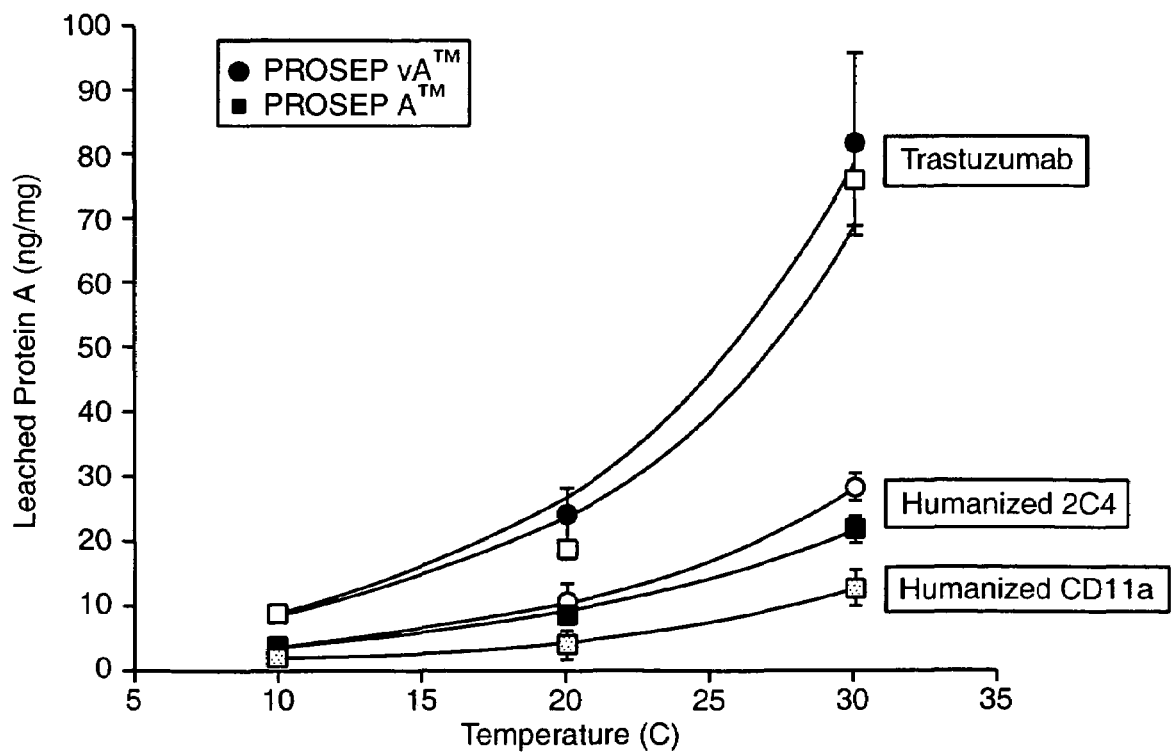
FIG._2

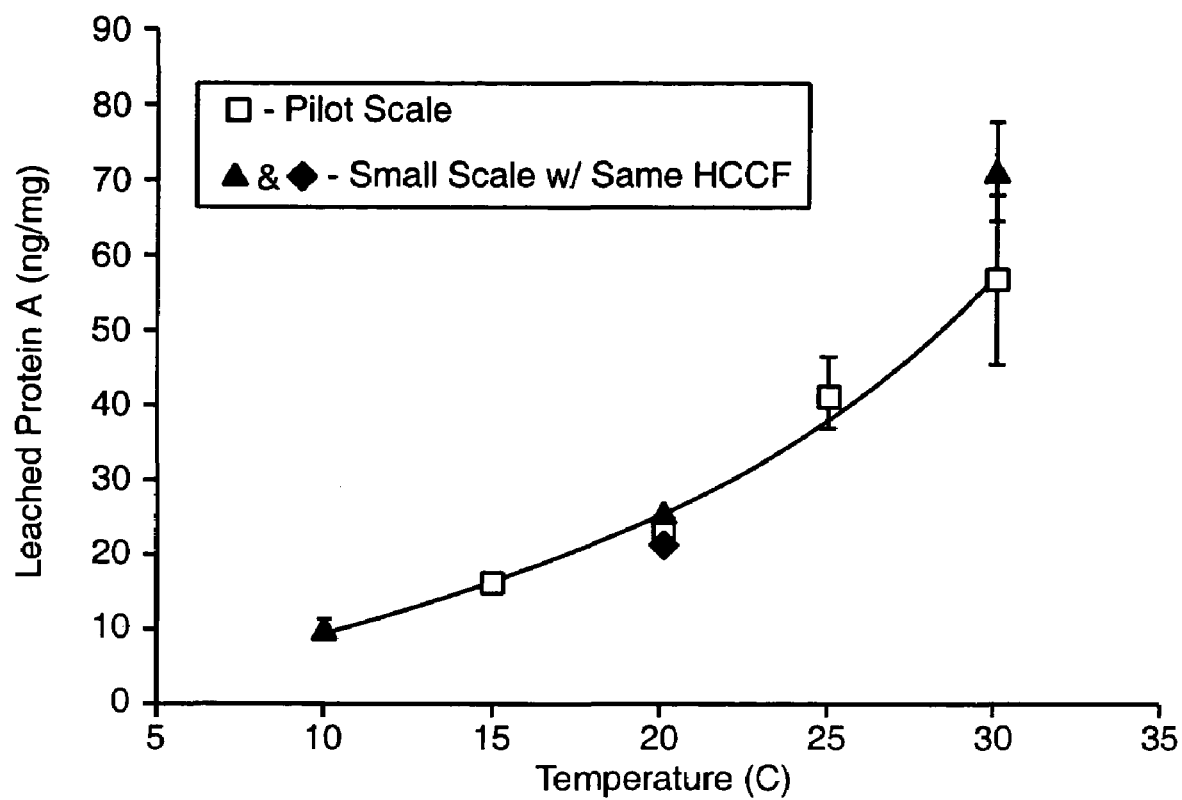
FIG._3

LIGHT CHAIN

```
1                15                30                45
D I Q M T Q S P S S L S A S V G D R V T I T C R A S Q D V N T A V A W Y Q Q K P G K A P K
46               60                75                90
L L I Y S A S F L Y S G V P S R F S G S R S G T D F T L T I S S L Q P E D F A T Y Y C Q Q
91              105               120               135
H Y T T P P T F G Q G T K V E I K R T V A A P S V F I F P P S D E Q L K S G T A S V V C L
136             150               165               180
L N N F Y P R E A K V Q W K V D N A L Q S G N S Q E S V T E Q D S K D S T Y S L S S T L T
181             195               210    214
L S K A D Y E K H K V Y A C E V T H Q G L S S P V T K S F N R G E C
```

(SEQ ID NO: 1)

FIG._4A

HEAVY CHAIN

```
  1                                            15                                             30                                            45
  E V Q L V E S G G G L V Q P G G S L R L S C A A S G F N I K D T Y I H W V R Q A P G K G L
 46                                            60                                             75                                            90
  E W V A R I Y P T N G Y T R Y A D S V K G R F T I S A D T S K N T A Y L Q M N S L R A E D
 91                                           105                                            120                                           135
  T A V Y Y C S R W G G D G F Y A M D Y W G Q G T L V T V S S A S T K G P S V F P L A P S S
136                                           150                                            165                                           180
  K S T S G G T A A L G C L V K D Y F P E P V T V S W N S G A L T S G V H T F P A V L Q S S
181                                           195                                            210                                           225
  G L Y S L S S V V T V P S S S L G T Q T Y I C N V N H K P S N T K V D K K V E P K S C D K
226                                           240                                            255                                           270
  T H T C P P C P A P E L L G G P S V F L F P P K P K D T L M I S R T P E V T C V V V D V S
271                                           285                                            300                                           315
  H E D P E V K F N W Y V D G V E V H N A K T K P R E E Q Y N S T Y R V V S V L T V L H Q D
316                                           330                                            345                                           360
  W L N G K E Y K C K V S N K A L P A P I E K T I S K A K G Q P R E P Q V Y T L P P S R E E
361                                           375                                            390                                           405
  M T K N Q V S L T C L V K G F Y P S D I A V E W E S N G Q P E N N Y K T T P P V L D S D G
406                                           420                                            435                                           449
  S F F L Y S K L T V D K S R W Q Q G N V F S C S V M H E A L H N H Y T Q K S L S L S P G
```

(SEQ ID NO: 2)

FIG._4B

DIQMTQSPSSLSASVGDRVTITCKASQDVSIGVAWYQQKPGKAPKLLIYSASYR
YTGVPSRFSGSGSGTDFTLTISSLQPEDFATYYCQQYYIYPYTFGQGTKVEIK

FIG._5A (SEQ ID NO: 3)

EVQLVESGGGLVQPGGSLRLSCAASGFTFTDYTMDWVRQAPGKGLEWVADVNPN
SGGSIYNQRFKGRFTLSVDRSKNTLYLQMNSLRAEDTAVYYCARNLGPSFYFDY
WGQGTLVTVSS

FIG._5B (SEQ ID NO: 4)

DIQMTQSPSSLSASVGDRVTITCRASKTISKYLAWYQQKPGKAPKLLIYSGSTL
QSGVPSRFSGSGSGTDFTLTISSLQPEDFATYYCQQHNEYPLTFGQGTKVEIKR

FIG._6A (SEQ ID NO: 5)

EVQLVESGGGLVQPGGSLRLSCAASGYSFTGHWMNWVRQAPGKGLEWVGMIHPS
DSETRYNQKFKDRFTISVDKSKNTLYLQMNSLRAEDTAVYYCARGIYFYGTTYF
DYWGQGTLVTVSS

FIG._6B (SEQ ID NO: 6)

DIQMTQSPSSLSASVGDRVTITCSASQDISNYLNWYQQKPGKAPKVLIYFTSSL
HSGVPSRFSGSGSGTDFTLTISSLQPEDFATYYCQQYSTVPWTFGQGTKVEIKR

FIG._7A (SEQ ID NO: 7)

EVQLVESGGGLVQPGGSLRLSCAASGYTFTNYGMNWVRQAPGKGLEWVGWINTY
TGEPTYAADFKRRFTFSLDTSKSTAYLQMNSLRAEDTAVYYCAKYPHYYGSSHW
YFDVWGQGTLVTVSS

FIG._7B (SEQ ID NO: 8)

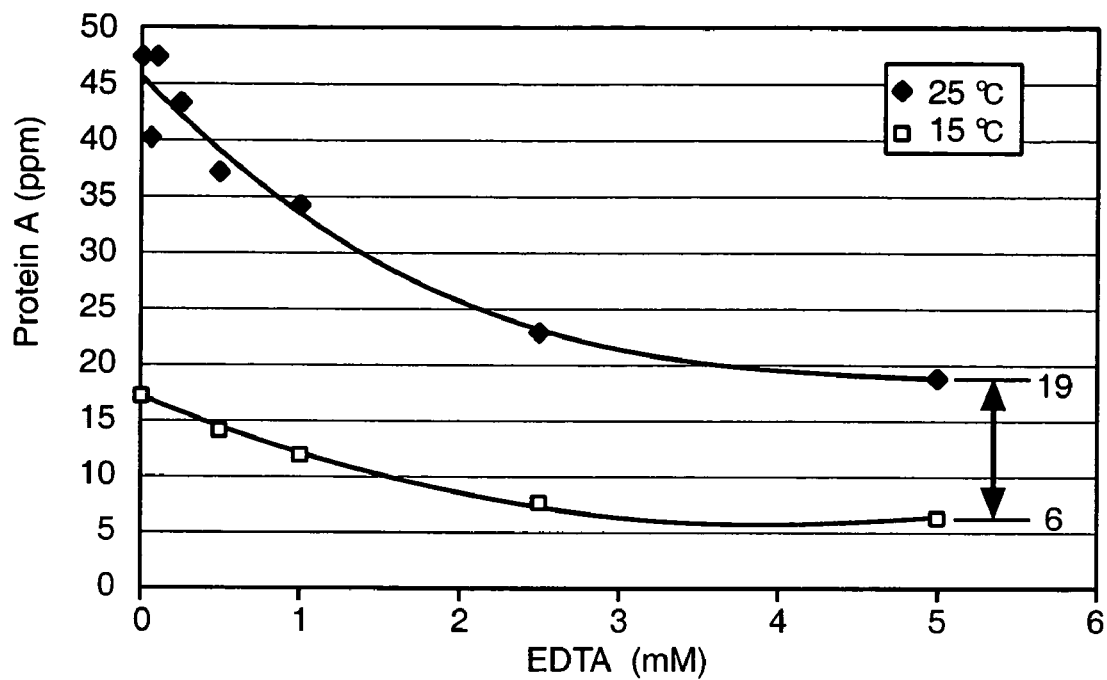
FIG._8
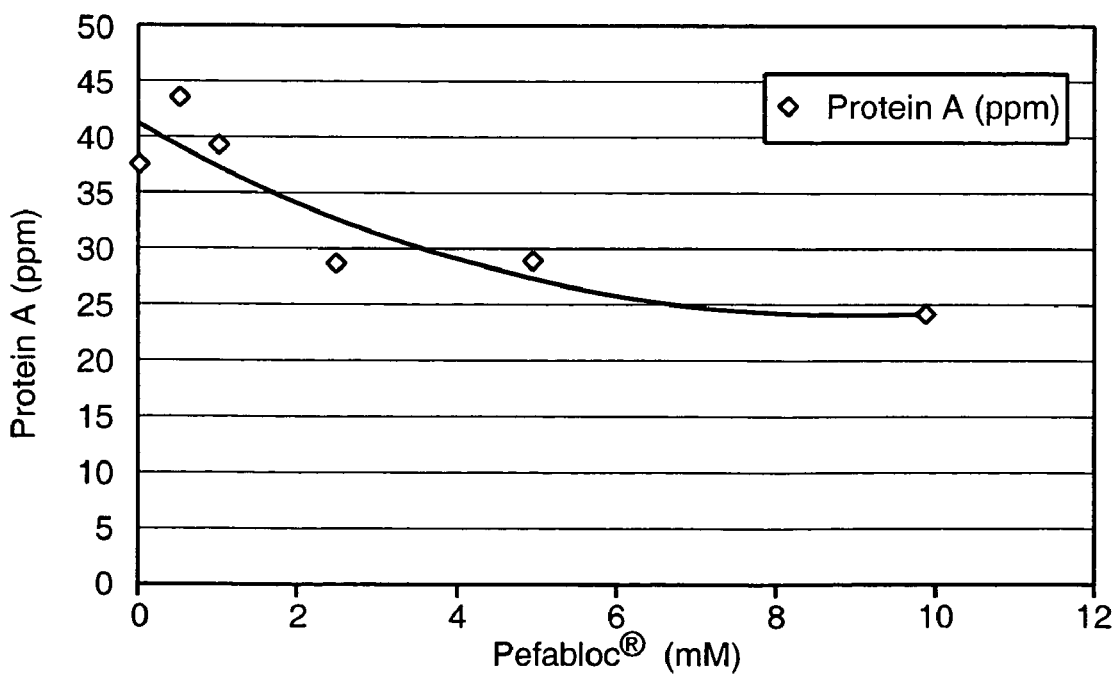
FIG._9

SEQUENCE LISTING

<160> NUMBER OF SEQ ID NOS: 8

<210> SEQ ID NO 1
<211> LENGTH: 214
<212> TYPE: PRT
<213> ORGANISM: Artificial sequence
<220> FEATURE:
<223> OTHER INFORMATION: sequence is synthesized

<400> SEQUENCE: 1

Asp Ile Gln Met Thr Gln Ser Pro Ser Ser Leu Ser Ala Ser Val
 1               5                  10                  15

Gly Asp Arg Val Thr Ile Thr Cys Arg Ala Ser Gln Asp Val Asn
                20                  25                  30

Thr Ala Val Ala Trp Tyr Gln Gln Lys Pro Gly Lys Ala Pro Lys
                35                  40                  45

Leu Leu Ile Tyr Ser Ala Ser Phe Leu Tyr Ser Gly Val Pro Ser
                50                  55                  60

Arg Phe Ser Gly Ser Arg Ser Gly Thr Asp Phe Thr Leu Thr Ile
                65                  70                  75

Ser Ser Leu Gln Pro Glu Asp Phe Ala Thr Tyr Tyr Cys Gln Gln
                80                  85                  90

His Tyr Thr Thr Pro Pro Thr Phe Gly Gln Gly Thr Lys Val Glu
                95                 100                 105

Ile Lys Arg Thr Val Ala Ala Pro Ser Val Phe Ile Phe Pro Pro
               110                 115                 120

Ser Asp Glu Gln Leu Lys Ser Gly Thr Ala Ser Val Val Cys Leu
               125                 130                 135

Leu Asn Asn Phe Tyr Pro Arg Glu Ala Lys Val Gln Trp Lys Val
               140                 145                 150

Asp Asn Ala Leu Gln Ser Gly Asn Ser Gln Glu Ser Val Thr Glu
               155                 160                 165

Gln Asp Ser Lys Asp Ser Thr Tyr Ser Leu Ser Ser Thr Leu Thr
               170                 175                 180

Leu Ser Lys Ala Asp Tyr Glu Lys His Lys Val Tyr Ala Cys Glu
               185                 190                 195

Val Thr His Gln Gly Leu Ser Ser Pro Val Thr Lys Ser Phe Asn
               200                 205                 210

Arg Gly Glu Cys

<210> SEQ ID NO 2
<211> LENGTH: 449
<212> TYPE: PRT
<213> ORGANISM: Artificial sequence
<220> FEATURE:
<223> OTHER INFORMATION: sequence is synthesized

<400> SEQUENCE: 2

Glu Val Gln Leu Val Glu Ser Gly Gly Gly Leu Val Gln Pro Gly
 1               5                  10                  15

Gly Ser Leu Arg Leu Ser Cys Ala Ala Ser Gly Phe Asn Ile Lys
                20                  25                  30

Asp Thr Tyr Ile His Trp Val Arg Gln Ala Pro Gly Lys Gly Leu
                35                  40                  45

Glu Trp Val Ala Arg Ile Tyr Pro Thr Asn Gly Tyr Thr Arg Tyr
                50                  55                  60

-continued

```
Ala Asp Ser Val Lys Gly Arg Phe Thr Ile Ser Ala Asp Thr Ser
                 65                   70                  75
Lys Asn Thr Ala Tyr Leu Gln Met Asn Ser Leu Arg Ala Glu Asp
                 80                   85                  90
Thr Ala Val Tyr Tyr Cys Ser Arg Trp Gly Gly Asp Gly Phe Tyr
                 95                  100                 105
Ala Met Asp Tyr Trp Gly Gln Gly Thr Leu Val Thr Val Ser Ser
                110                  115                 120
Ala Ser Thr Lys Gly Pro Ser Val Phe Pro Leu Ala Pro Ser Ser
                125                  130                 135
Lys Ser Thr Ser Gly Gly Thr Ala Ala Leu Gly Cys Leu Val Lys
                140                  145                 150
Asp Tyr Phe Pro Glu Pro Val Thr Val Ser Trp Asn Ser Gly Ala
                155                  160                 165
Leu Thr Ser Gly Val His Thr Phe Pro Ala Val Leu Gln Ser Ser
                170                  175                 180
Gly Leu Tyr Ser Leu Ser Ser Val Val Thr Val Pro Ser Ser Ser
                185                  190                 195
Leu Gly Thr Gln Thr Tyr Ile Cys Asn Val Asn His Lys Pro Ser
                200                  205                 210
Asn Thr Lys Val Asp Lys Lys Val Glu Pro Lys Ser Cys Asp Lys
                215                  220                 225
Thr His Thr Cys Pro Pro Cys Pro Ala Pro Glu Leu Leu Gly Gly
                230                  235                 240
Pro Ser Val Phe Leu Phe Pro Pro Lys Pro Lys Asp Thr Leu Met
                245                  250                 255
Ile Ser Arg Thr Pro Glu Val Thr Cys Val Val Val Asp Val Ser
                260                  265                 270
His Glu Asp Pro Glu Val Lys Phe Asn Trp Tyr Val Asp Gly Val
                275                  280                 285
Glu Val His Asn Ala Lys Thr Lys Pro Arg Glu Glu Gln Tyr Asn
                290                  295                 300
Ser Thr Tyr Arg Val Val Ser Val Leu Thr Val Leu His Gln Asp
                305                  310                 315
Trp Leu Asn Gly Lys Glu Tyr Lys Cys Lys Val Ser Asn Lys Ala
                320                  325                 330
Leu Pro Ala Pro Ile Glu Lys Thr Ile Ser Lys Ala Lys Gly Gln
                335                  340                 345
Pro Arg Glu Pro Gln Val Tyr Thr Leu Pro Pro Ser Arg Glu Glu
                350                  355                 360
Met Thr Lys Asn Gln Val Ser Leu Thr Cys Leu Val Lys Gly Phe
                365                  370                 375
Tyr Pro Ser Asp Ile Ala Val Glu Trp Glu Ser Asn Gly Gln Pro
                380                  385                 390
Glu Asn Asn Tyr Lys Thr Thr Pro Pro Val Leu Asp Ser Asp Gly
                395                  400                 405
Ser Phe Phe Leu Tyr Ser Lys Leu Thr Val Asp Lys Ser Arg Trp
                410                  415                 420
Gln Gln Gly Asn Val Phe Ser Cys Ser Val Met His Glu Ala Leu
                425                  430                 435
His Asn His Tyr Thr Gln Lys Ser Leu Ser Leu Ser Pro Gly
                440                  445
```

```
<210> SEQ ID NO 3
<211> LENGTH: 107
<212> TYPE: PRT
<213> ORGANISM: Artificial sequence
<220> FEATURE:
<223> OTHER INFORMATION: sequence is synthesized

<400> SEQUENCE: 3

Asp Ile Gln Met Thr Gln Ser Pro Ser Ser Leu Ser Ala Ser Val
 1               5                  10                  15

Gly Asp Arg Val Thr Ile Thr Cys Lys Ala Ser Gln Asp Val Ser
                20                  25                  30

Ile Gly Val Ala Trp Tyr Gln Gln Lys Pro Gly Lys Ala Pro Lys
            35                  40                  45

Leu Leu Ile Tyr Ser Ala Ser Tyr Arg Tyr Thr Gly Val Pro Ser
        50                  55                  60

Arg Phe Ser Gly Ser Gly Ser Gly Thr Asp Phe Thr Leu Thr Ile
 65                  70                  75

Ser Ser Leu Gln Pro Glu Asp Phe Ala Thr Tyr Tyr Cys Gln Gln
                80                  85                  90

Tyr Tyr Ile Tyr Pro Tyr Thr Phe Gly Gln Gly Thr Lys Val Glu
                95                 100                 105

Ile Lys

<210> SEQ ID NO 4
<211> LENGTH: 119
<212> TYPE: PRT
<213> ORGANISM: Artificial sequence
<220> FEATURE:
<223> OTHER INFORMATION: sequence is synthesized

<400> SEQUENCE: 4

Glu Val Gln Leu Val Glu Ser Gly Gly Gly Leu Val Gln Pro Gly
 1               5                  10                  15

Gly Ser Leu Arg Leu Ser Cys Ala Ala Ser Gly Phe Thr Phe Thr
                20                  25                  30

Asp Tyr Thr Met Asp Trp Val Arg Gln Ala Pro Gly Lys Gly Leu
            35                  40                  45

Glu Trp Val Ala Asp Val Asn Pro Asn Ser Gly Gly Ser Ile Tyr
        50                  55                  60

Asn Gln Arg Phe Lys Gly Arg Phe Thr Leu Ser Val Asp Arg Ser
 65                  70                  75

Lys Asn Thr Leu Tyr Leu Gln Met Asn Ser Leu Arg Ala Glu Asp
                80                  85                  90

Thr Ala Val Tyr Tyr Cys Ala Arg Asn Leu Gly Pro Ser Phe Tyr
                95                 100                 105

Phe Asp Tyr Trp Gly Gln Gly Thr Leu Val Thr Val Ser Ser
                110                 115

<210> SEQ ID NO 5
<211> LENGTH: 108
<212> TYPE: PRT
<213> ORGANISM: Artificial sequence
<220> FEATURE:
<223> OTHER INFORMATION: sequence is synthesized
```

```
<400> SEQUENCE: 5

Asp Ile Gln Met Thr Gln Ser Pro Ser Ser Leu Ser Ala Ser Val
 1               5                  10                  15

Gly Asp Arg Val Thr Ile Thr Cys Arg Ala Ser Lys Thr Ile Ser
                20                  25                  30

Lys Tyr Leu Ala Trp Tyr Gln Gln Lys Pro Gly Lys Ala Pro Lys
                35                  40                  45

Leu Leu Ile Tyr Ser Gly Ser Thr Leu Gln Ser Gly Val Pro Ser
                50                  55                  60

Arg Phe Ser Gly Ser Gly Ser Gly Thr Asp Phe Thr Leu Thr Ile
 65                  70                  75

Ser Ser Leu Gln Pro Glu Asp Phe Ala Thr Tyr Tyr Cys Gln Gln
                80                  85                  90

His Asn Glu Tyr Pro Leu Thr Phe Gly Gln Gly Thr Lys Val Glu
                95                 100                 105

Ile Lys Arg

<210> SEQ ID NO 6
<211> LENGTH: 121
<212> TYPE: PRT
<213> ORGANISM: Artificial sequence
<220> FEATURE:
<223> OTHER INFORMATION: sequence is synthesized

<400> SEQUENCE: 6

Glu Val Gln Leu Val Glu Ser Gly Gly Gly Leu Val Gln Pro Gly
 1               5                  10                  15

Gly Ser Leu Arg Leu Ser Cys Ala Ala Ser Gly Tyr Ser Phe Thr
                20                  25                  30

Gly His Trp Met Asn Trp Val Arg Gln Ala Pro Gly Lys Gly Leu
                35                  40                  45

Glu Trp Val Gly Met Ile His Pro Ser Asp Ser Glu Thr Arg Tyr
                50                  55                  60

Asn Gln Lys Phe Lys Asp Arg Phe Thr Ile Ser Val Asp Lys Ser
 65                  70                  75

Lys Asn Thr Leu Tyr Leu Gln Met Asn Ser Leu Arg Ala Glu Asp
                80                  85                  90

Thr Ala Val Tyr Tyr Cys Ala Arg Gly Ile Tyr Phe Tyr Gly Thr
                95                 100                 105

Thr Tyr Phe Asp Tyr Trp Gly Gln Gly Thr Leu Val Thr Val Ser
               110                 115                 120

Ser

<210> SEQ ID NO 7
<211> LENGTH: 108
<212> TYPE: PRT
<213> ORGANISM: Artificial sequence
<220> FEATURE:
<223> OTHER INFORMATION: sequence is synthesized

<400> SEQUENCE: 7

Asp Ile Gln Met Thr Gln Ser Pro Ser Ser Leu Ser Ala Ser Val
 1               5                  10                  15

Gly Asp Arg Val Thr Ile Thr Cys Ser Ala Ser Gln Asp Ile Ser
                20                  25                  30

Asn Tyr Leu Asn Trp Tyr Gln Gln Lys Pro Gly Lys Ala Pro Lys
                35                  40                  45
```

-continued

```
Val Leu Ile Tyr Phe Thr Ser Ser Leu His Ser Gly Val Pro Ser
                 50                  55                  60

Arg Phe Ser Gly Ser Gly Ser Gly Thr Asp Phe Thr Leu Thr Ile
                 65                  70                  75

Ser Ser Leu Gln Pro Glu Asp Phe Ala Thr Tyr Tyr Cys Gln Gln
                 80                  85                  90

Tyr Ser Thr Val Pro Trp Thr Phe Gly Gln Gly Thr Lys Val Glu
                 95                 100                 105

Ile Lys Arg

<210> SEQ ID NO 8
<211> LENGTH: 123
<212> TYPE: PRT
<213> ORGANISM: Artificial sequence
<220> FEATURE:
<223> OTHER INFORMATION: sequence is synthesized

<400> SEQUENCE: 8

Glu Val Gln Leu Val Glu Ser Gly Gly Gly Leu Val Gln Pro Gly
 1               5                  10                  15

Gly Ser Leu Arg Leu Ser Cys Ala Ala Ser Gly Tyr Thr Phe Thr
                 20                  25                  30

Asn Tyr Gly Met Asn Trp Val Arg Gln Ala Pro Gly Lys Gly Leu
                 35                  40                  45

Glu Trp Val Gly Trp Ile Asn Thr Tyr Thr Gly Glu Pro Thr Tyr
                 50                  55                  60

Ala Ala Asp Phe Lys Arg Arg Phe Thr Phe Ser Leu Asp Thr Ser
                 65                  70                  75

Lys Ser Thr Ala Tyr Leu Gln Met Asn Ser Leu Arg Ala Glu Asp
                 80                  85                  90

Thr Ala Val Tyr Tyr Cys Ala Lys Tyr Pro His Tyr Tyr Gly Ser
                 95                 100                 105

Ser His Trp Tyr Phe Asp Val Trp Gly Gln Gly Thr Leu Val Thr
                110                 115                 120

Val Ser Ser
```

US 7,485,704 B2

REDUCING PROTEIN A LEACHING DURING PROTEIN A AFFINITY CHROMATOGRAPHY

This is a non-provisional application claiming priority under 35 USC §119 to provisional application No. 60/490,500 filed Jul. 28, 2003, the entire disclosure of which is hereby incorporated by reference.

BACKGROUND OF THE INVENTION

1. Field of the Invention

The present invention concerns protein purification. In particular, the invention concerns a method for reducing leaching of protein A during protein A affinity chromatography by reducing temperature or pH of, or by adding one or more protease inhibitors to, a composition that is subjected to protein A affinity chromatography.

2. Description of Related Art

The large-scale, economic purification of proteins is increasingly an important problem for the biotechnology industry. Generally, proteins are produced by cell culture, using either mammalian or bacterial cell lines engineered to produce the protein of interest by insertion of a recombinant plasmid containing the gene for that protein. Since the cell lines used are living organisms, they must be fed with a complex growth medium, containing sugars, amino acids, and growth factors, usually supplied from preparations of animal serum. Separation of the desired protein from the mixture of compounds fed to the cells and from the by-products of the cells themselves to a purity sufficient for use as a human therapeutic poses a formidable challenge.

Procedures for purification of proteins from cell debris initially depend on the site of expression of the protein. Some proteins can be caused to be secreted directly from the cell into the surrounding growth media; others are made intracellularly. For the latter proteins, the first step of a purification process involves lysis of the cell, which can be done by a variety of methods, including mechanical shear, osmotic shock, or enzymatic treatments. Such disruption releases the entire contents of the cell into the homogenate, and in addition produces subcellular fragments that are difficult to remove due to their small size. These are generally removed by differential centrifugation or by filtration. The same problem arises, although on a smaller scale, with directly secreted proteins due to the natural death of cells and release of intracellular host cell proteins in the course of the protein production run.

Once a clarified solution containing the protein of interest has been obtained, its separation from the other proteins produced by the cell is usually attempted using a combination of different chromatography techniques. These techniques separate mixtures of proteins on the basis of their charge, degree of hydrophobicity, or size. Several different chromatography resins are available for each of these techniques, allowing accurate tailoring of the purification scheme to the particular protein involved. The essence of each of these separation methods is that proteins can be caused either to move at different rates down a long column, achieving a physical separation that increases as they pass further down the column, or to adhere selectively to the separation medium, being then differentially eluted by different solvents. In some cases, the desired protein is separated from impurities when the impurities specifically adhere to the column, and the protein of interest does not, that is, the protein of interest is present in the "flow-through."

Affinity chromatography, which exploits a specific interaction between the protein to be purified and an immobilized capture agent, may also be an option for some proteins. Protein A is a useful adsorbent for affinity chromatography of proteins, such as antibodies, which contain an Fc region. Protein A is a 41 kD cell wall protein from *Staphylococcus aureas* which binds with a high affinity (about $10^{-8}$M to human IgG) to the Fc region of antibodies.

U.S. Pat. Nos. 6,127,526 and 6,333,398 (Blank, G.) describe an intermediate wash step during protein A affinity chromatography using hydrophobic electrolytes, e.g., tetramethylammonium chloride (TMAC) and tetraethylammonium chloride (TEAC), to remove the impurities, but not the immobilized protein A or the protein of interest, bound to the protein A column.

SUMMARY OF THE INVENTION

The present invention concerns a method of purifying a protein which comprises a $C_H2/C_H3$ region, comprising reducing the temperature of a composition comprising the protein and one or more impurities subjected to protein A affinity chromatography in the range from about 3° C. to about 20° C., wherein protein A leaching is reduced.

Preferably the protein is an antibody, e.g. one which binds an antigen selected from the group consisting of HER2, vascular endothelial growth factor (VEGF), IgE, CD20, CD40, CD11a, tissue factor (TF), prostate stem cell antigen (PSCA), interleukin-8 (IL-8), epidermal growth factor receptor (EGFR), HER3, HER4, α4β7 or α5β3. In another embodiment, the protein is an immunoadhesin, such as a TNF receptor immunoadhesin.

The invention also concerns a method of purifying a protein which comprises a $C_H2/C_H3$ region by protein A affinity chromatography comprising:
(a) subjecting the protein to protein A affinity chromatography and measuring leached protein A in a composition comprising the protein which is recovered from the protein A affinity chromatography;
(b) if protein A leaching is detected in step (a), reducing the temperature of a composition comprising the protein and one or more impurities subjected to protein A affinity chromatography in the range from about 3° C. to about 20° C., such that protein A leaching is reduced.

The invention further provides a method for reducing leaching of protein A during protein A affinity chromatography comprising reducing protease activity in a composition subjected to protein A affinity chromatography, wherein the composition comprises a protein which comprises a $C_H2/C_H3$ region and one or more proteases.

BRIEF DESCRIPTION OF THE DRAWINGS

FIG. 1 depicts protein A leaching as a function of temperature for various antibody products on PROSEP A™. Leached protein A is shown in ng/mg (ng protein A per mg antibody). Temperature on the x-axis refers to the temperature of the water bath. The column was equilibrated and washed with 25 mM Tris, 25 mM NaCl, 5 mM EDTA, pH 7.1, washed with 25 mM Tris, 25 mM NaCl, 0.5 M TMAC, 5 mM EDTA pH 5.0 or 7.1, eluted with either 25 mM citrate pH 2.8, or 0.1 M acetic acid pH 2.9, regenerated with 0.1 M phosphoric acid, and stored in 0.2 M sodium acetate, 2% benzyl alcohol pH 5.0. Trastuzumab was run on a bed height of 20 cm, loaded to 20 g Trastuzumab/L resin, washed with TMAC pH 5.0, eluted with 25 mM citrate pH 2.8, and pooled from 0.1 AU to 2 CV's. Humanized 2C4 was run on a 20 cm bed height column, loaded to 15 g humanized 2C4 per liter resin, washed with TMAC pH 7.1, eluted with 25 mM citrate pH 2.8, and pooled from 0.1 AU to 2 CV's pool volume. Humanized VEGF antibody was run on 14 cm bed height, loaded to 20 g humanized VEGF antibody per liter of resin, washed with TMAC pH 5.0, eluted with 0.1M acetic acid pH 2.9, and pooled from 0.2 AU to 2 CV's pool volume. Humanized CD11a antibody was run on a 14 cm bed height, loaded to 20 g humanized CD11a antibody per liter of resin, washed with TMAC pH 7.1, eluted with 0.1 M acetic acid pH 2.9, and pooled from 0.2 AU to 2CV's.

FIG. 2 depicts a comparison of temperature dependent protein A leaching from PROSEP A™ and PROSEP vA™ with Trastuzumab, humanized 2C4, and humanized CD11a antibody. Leached protein A is shown in ng/mg (ng protein A per mg antibody). Temperature on the x-axis refers to the temperature of the water bath. All columns were 0.66 cm in diameter and either 14 cm or 20 cm in height. One lot of harvested cell culture fluid (HCCF) was used for each pair of runs. The column was equilibrated and washed with 25 mM Tris, 25 mM NaCl, 5 mM EDTA, pH 7.1, washed with 25 mM Tris, 25 mM NaCl, 0.5 M TMAC, 5 mM EDTA pH 5.0 or 7.1, eluted with either 25 mM citrate pH 2.8, or 0.1 M acetic acid pH 2.9, regenerated with 0.1 M phosphoric acid, and stored in 0.2 M sodium acetate, 2% benzyl alcohol pH 5.0 at 40 CV/hr. Humanized CD11a antibody was run on a 14 cm bed height, loaded to 20 g humanized CD11a antibody per liter of resin, washed with TMAC pH 7.1, eluted with 0.1 M acetic acid pH 2.9, and pooled from 0.2 AU to 2CV's. Humanized 2C4 was run on a 20 cm bed height column, loaded to 15 g humanized 2C4 per liter resin, washed with TMAC pH 7.1, eluted with 25 mM citrate pH 2.8, and pooled from 0.1 AU to 2 CV's pool volume. Trastuzumab (from pilot plant at 400L scale at concentration of 0.57 mg/ml) was run on a bed height of 20 cm, loaded to 20 g Trastuzumab/L resin, washed with TMAC pH 5.0, eluted with 25 mM citrate pH 2.8, and pooled from 0.1 AU to 2 CV's.

FIG. 3 depicts protein A leaching at pilot scale versus temperature. Leached protein A is shown in ng/mg (ng protein A per mg antibody). Temperature on the x-axis refers to the set temperature of the HCCF tank. The column was packed with 1.26 L PROSEP vA™, 9 cm in diameter by 20 cm in height. Trastuzumab HCCF was at 0.59 mg/ml, and the temperature of the HCCF in the tank was maintained at 10, 15, 20, 25, or 30° C. The column was loaded to 20 g Trastuzumab per liter of resin. Temperature was measured in the HCCF tank, between the pump and the column, and at the outlet to the column. The column was equilibrated and washed with 25 mM Tris, 25 mM NaCl, 5 mM EDTA, pH 7.1, washed with 25 mM Tris, 25 mM NaCl, 0.5 M TMAC, 5 mM EDTA pH 5.0, eluted with either 25 mM citrate pH 2.8, regenerated with 0.1 M phosphoric acid, and stored in 0.2 M sodium acetate, 2% benzyl alcohol pH 5.0. A sample of each HCCF was taken and run at lab scale on a 0.66 cm diameter by 20 cm high column packed with PROSEP vA™ using the same buffers as at pilot scale, represented on the graph by the circles.

FIGS. 4A-B show the light chain amino acid sequence (SEQ ID NO:1) and heavy chain amino acid sequence (SEQ ID NO:2), respectively, of Trastuzumab (HERCEPTIN®).

FIGS. 5A-B depict the amino acid sequences of the variable light (SEQ ID NO:3) and variable heavy (SEQ ID NO:4) domains, respectively, of a humanized 2C4.

FIGS. 6A-B depict the amino acid sequences of the variable light (SEQ ID NO:5) and variable heavy (SEQ ID NO:6) domains, respectively, of a humanized CD11a antibody RAPTIVA™.

FIGS. 7A-B depict the amino acid sequences of the variable light (SEQ ID NO:7) and variable heavy (SEQ ID NO:8) domains, respectively, of a humanized VEGF antibody AVASTIN™.

FIG. 8 depicts the effect of EDTA and temperature on Protein A leaching.

FIG. 9 depicts the effect of 4-(2-aminoethyl)-benzenesulfonyl-fluoride, hydrochloride (AEBSF) (PEFABLOC®), a serine protease inhibitor, on Protein A leaching

DETAILED DESCRIPTION OF THE PREFERRED EMBODIMENTS

Definitions:

When used herein, the term "protein A" encompasses protein A recovered from a native source thereof, protein A produced synthetically (e.g. by peptide synthesis or by recombinant techniques), including variants or derivatives thereof which retain the ability to bind proteins which have a $C_H2/C_H3$ region. Protein A can be purchased commercially from Repligen, Pharmacia and Fermatech.

"Protein A affinity chromatography" refers to the separation or purification of substances and/or particles using protein A, where the protein A is generally immobilized on a solid phase. A protein comprising a $C_H2/C_H3$ region may be reversibly bound to, or adsorbed by, the protein A. Examples of protein A affinity chromatography columns for use in protein A affinity chromatography herein include protein A immobilized onto a controlled pore glass backbone, including the PROSEP A™ and PROSEP vA™ columns (Millipore Inc.); protein A immobilized on a polystyrene solid phase, e.g. the POROS 50A™ column (Applied BioSystems Inc.); or protein A immobilized on an agarose solid phase, for instance the rPROTEIN A SEPHAROSE FAST FLOW™ or MABSELECT™ columns (Amersham Biosciences Inc.).

By "solid phase" is meant a non-aqueous matrix to which the protein A can adhere or be covalently bound. The solid phase may comprise a glass, silica, polystyrene, or agarose surface for immobilizing the protein A, for instance. The solid phase may be a purification column, discontinuous phase of discrete particles, packed bed column, expanded bed column, membrane, etc.

Herein, "leaching" refers to the detachment or washing of protein A (including fragments thereof) from a solid phase to which it is bound. Leaching may result from various mechanisms such as mechanical shearing, low pH exposure, proteolytic activity etc.

An "impurity" is a material that is different from the desired protein product. The impurity may be a viral impurity, a variant of the desired protein or another protein, nucleic acid, endotoxin etc. Specific examples of impurities herein include proteins from the host cell producing the desired protein (e.g. Chinese Hamster Ovary proteins, CHOP, where the host cell is a CHO cell), protease(s), leached protein A etc.

"Proteases" are proteolytic enzymes including, but not limited to, serine, cysteine, metallo- and aspartic proteases. Proteases present in a composition comprising a protein of interest may be derived from a recombinant host producing the protein, or from a natural source of the protein. Examples of proteases include thermolysin, trypsin, chymotrypsin, plasmin, kallikrein, thrombin, papain, plasmin, cathepsin B, renin, chymosin etc.

"Protease activity" refers to the enzymatic activity of one or more proteases. Such activity may be measured indirectly by measuring leaching of protein A, for instance. The activity may be reduced by reducing temperature of a composition comprising the protease(s), and/or by adding one or more protease inhibitors to the composition etc.

A "protease inhibitor" is a compound or composition which reduces, to some extent, the enzymatic activity of protease(s). Examples of protease inhibitors include phenylmethylsulfonyl fluoride (PMSF), 4-(2-aminoethyl)-benzenesulfonyl-fluoride, hydrochloride (AEBSF) (PEFABLOC® SC), leupeptin, pepstatin, benzamidine, a metal ion chelator such as EDTA or imidazole for inhibiting metalloprotease activity etc. The preferred protease inhibitors inhibit metalloprotease activity (e.g. EDTA) and/or inhibit certain serine protease activities.

The protein of interest herein is one which comprises a $C_H2/C_H3$ region and therefore is amenable to purification by protein A affinity chromatography. The term "$C_H2/C_H3$ region" when used herein refers to those amino acid residues in the Fc region of an immunoglobulin molecule which interact with protein A. In preferred embodiments, the $C_H2/C_H3$ region comprises an intact $C_H2$ region followed by an intact $C_H3$ region, and most preferably comprises a Fc region of an immunoglobulin. Examples of $C_H2/C_H3$ region-containing proteins include antibodies, immunoadhesins and fusion proteins comprising a protein of interest fused to, or conjugated with, a $C_H2/C_H3$ region.

The term "antibody" is used in the broadest sense and specifically covers monoclonal antibodies (including full length monoclonal antibodies), polyclonal antibodies, multispecific antibodies (e.g., bispecific antibodies), and antibody fragments so long as they retain, or are modified to comprise, a $C_H2/C_H3$ region as herein defined.

"Antibody fragments" comprise a portion of a full length antibody, generally the antigen binding or variable region thereof. Examples of antibody fragments include Fab, Fab', F(ab')$_2$, and Fv fragments; single-chain antibody molecules; diabodies; linear antibodies; and multispecific antibodies formed from antibody fragments.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., Nature 256:495 (1975), or may be made by recombinant DNA methods (see, e.g., U.S. Pat. No. 4,816,567). The "monoclonal antibodies" may also be isolated from phage antibody libraries using the techniques described in Clackson et al., Nature 352:624-628 (1991) and Marks et al., J. Mol. Biol. 222:581-597 (1991), for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA 81:6851-6855 (1984)).

The term "hypervariable region" when used herein refers to the amino acid residues of an antibody which are responsible for antigen-binding. The hypervariable region comprises amino acid residues from a "complementarity determining region" or "CDR" (i.e. residues 24-34 (L1), 50-56 (L2) and 89-97 (L3) in the light chain variable domain and 31-35 (H1), 50-65 (H2) and 95-102 (H3) in the heavy chain variable domain; Kabat et al., Sequences of Proteins of Immunological Interest, 5th Ed. Public Health Service, National Institutes of Health, Bethesda, Md. (1991)) and/or those residues from a "hypervariable loop" (i.e. residues 26-32 (L1), 50-52 (L2) and 91-96 (L3) in the light chain variable domain and 26-32 (H1), 53-55 (H2) and 96-101 (H3) in the heavy chain variable domain; Chothia and Lesk J. Mol. Biol. 196: 901-917 (1987)). "Framework" or "FR" residues are those variable domain residues other than the hypervariable region residues as herein defined.

"Humanized" forms of non-human (e.g., murine) antibodies are chimeric antibodies which contain minimal sequence derived from non-human immunoglobulin. For the most part, humanized antibodies are human immunoglobulins (recipient antibody) in which hypervariable region residues of the recipient are replaced by hypervariable region residues from a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues which are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. For further details, see Jones et al., Nature 321:522-525 (1986); Riechmann et al., Nature 332: 323-329 (1988); and Presta, Curr. Op. Struct. Biol. 2:593-596 (1992).

As used herein, the term "immunoadhesin" designates antibody-like molecules which combine the "binding domain" of a heterologous "adhesin" protein (e.g. a receptor, ligand or enzyme) with the effector functions of an immunoglobulin constant domain. Structurally, the immunoadhesins comprise a fusion of the adhesin amino acid sequence with the desired binding specificity which is other than the antigen recognition and binding site (antigen combining site) of an antibody (i.e. is "heterologous") and an immunoglobulin constant domain sequence. The immunoglobulin constant domain sequence in the immunoadhesin is preferably derived from γ1, γ2, or γ4 heavy chains since immunoadhesins comprising these regions can be purified by protein A affinity chromatography (Lindmark et al., J. Immunol. Meth. 62:1-13 (1983)).

The term "ligand binding domain" as used herein refers to any native cell-surface receptor or any region or derivative thereof retaining at least a qualitative ligand binding of a corresponding native receptor. In a specific embodiment, the receptor is from a cell-surface polypeptide having an extracellular domain which is homologous to a member of the immunoglobulin supergenefamily. Other receptors, which are not members of the immunoglobulin supergenefamily but are nonetheless specifically covered by this definition, are receptors for cytokines, and in particular receptors with tyrosine kinase activity (receptor tyrosine kinases), members of the hematopoietin and nerve growth factor receptor superfamilies, and cell adhesion molecules, e.g. (E-, L- and P-) selectins.

The term "receptor binding domain" is used to designate any native ligand for a receptor, including cell adhesion molecules, or any region or derivative of such native ligand retaining at least a qualitative receptor binding ability of a corresponding native ligand. This definition, among others, specifically includes binding sequences from ligands for the above-mentioned receptors. An "antibody-immunoadhesin chimera" comprises a molecule which combines at least one binding domain of an antibody (as herein defined) with at least one immunoadhesin (as defined in this application). Exemplary antibody-immunoadhesin chimeras are the bispecific CD4-IgG chimeras described in Berg et al., *PNAS (USA)* 88:4723-4727 (1991) and Chamow et al., *J. Immunol.* 153: 4268 (1994).

The expression "HER2" refers to human HER2 protein described, for example, in Semba et al., *PNAS (USA)* 82:6497-6501 (1985) and Yamamoto et al. *Nature* 319:230-234 (1986) (Genebank accession number X03363).

"Trastuzumab" or "HERCEPTIN®" is a humanized HER2 antibody comprising the light chain amino acid sequence of SEQ ID NO:1 and the heavy chain amino acid sequence of SEQ ID NO:2, or amino acid sequence variants thereof which retain the ability to bind HER2 and inhibit growth of tumor cells which overexpress HER2 (see U.S. Pat. No. 5,677,171; expressly incorporated herein by reference).

"Humanized 2C4" is a humanized HER2 antibody comprising the variable light amino acid sequence of SEQ ID NO:3 and the variable heavy amino acid sequence of SEQ ID NO:4, or amino acid sequence variants thereof which retain the ability to bind HER2 and block ligand activation of HER2 (see WO01/00245; expressly incorporated herein by reference).

Modes for Carrying Out the Invention

The process herein involves purifying a $C_H2/C_H3$ region-containing protein from impurities by protein A affinity chromatography. In preferred embodiments, the protein is an antibody, immunoadhesin or a protein fused to, or conjugated with, a $C_H2/C_H3$ region. Techniques for generating such molecules will be discussed below.

1. Antibodies

The preferred protein according to the present invention is an antibody. Antibodies within the scope of the present invention include, but are not limited to: anti-HER2 antibodies including Trastuzumab (HERCEPTIN®) (Carter et al., *Proc. Natl. Acad. Sci. USA,* 89:4285-4289 (1992), U.S. Pat. No. 5,725,856) and humanized 2C4 (WO01/00245, Adams et al.); anti-CD20 antibodies such as chimeric anti-CD20 "C2B8" as in U.S. Pat. No. 5,736,137 (RITUXAN®), a chimeric or humanized variant of the 2H7 antibody as in U.S. Pat. No. 5,721,108B1, or Tositumomab (BEXXAR®); anti-IL-8 antibodies (St John et al., *Chest,* 103:932 (1993), and International Publication No. WO 95/23865); anti-VEGF antibodies, including humanized and/or affinity matured anti-VEGF antibodies such as the humanized anti-VEGF antibody huA4.6.1 AVASTIN® (Kim et al., *Growth Factors,* 7:53-64 (1992), International Publication No. WO 96/30046, and WO 98/45331, published Oct. 15, 1998); anti-prostate stem cell antigen (PSCA) antibodies (WO01/40309); anti-CD40 antibodies, including S2C6 and humanized variants thereof (WO00/75348); anti-CD11a antibodies (U.S. Pat. No. 5,622, 700, WO 98/23761, Steppe et al., *Transplant Intl.* 4:3-7 (1991), and Hourmant et al., *Transplantation* 58:377-380 (1994)); anti-CD18 (U.S. Pat. No. 5,622,700, issued Apr. 22, 1997, or as in WO 97/26912, published Jul. 31, 1997); anti-IgE antibodies (including E25, E26 and E27; U.S. Pat. No. 5,714,338, issued Feb. 3, 1998 or U.S. Pat. No. 5,091,313, issued Feb. 25, 1992, WO 93/04173 published Mar. 4, 1993, or International Application No. PCT/US98/13410 filed Jun. 30, 1998, U.S. Pat. No. 5,714,338, Presta et al., *J. Immunol.* 151:2623-2632 (1993), and International Publication No. WO 95/19181); anti-Apo-2 receptor antibodies (WO 98/51793 published Nov. 19, 1998); anti-TNF-α antibodies, including cA2 (REMICADE®), CDP571 and MAK-195 (See, U.S. Pat. No. 5,672,347 issued Sep. 30, 1997, Lorenz et al. *J. Immunol.* 156(4):1646-1653(1996), and Dhainaut et al. *Crit. Care Med.* 23(9):1461-1469 (1995)); anti-Tissue Factor (TF) antibodies (European Patent No. 0 420 937 B1 granted Nov. 9, 1994); anti-human $α_4β_7$ integrin antibodies (WO 98/06248 published Feb. 19, 1998); anti-epidermal growth factor receptor (EGFR) antibodies (e.g. chimerized or humanized 225 antibody as in WO 96/40210 published Dec. 19, 1996); anti-CD3 antibodies such as OKT3 (U.S. Pat. No. 4,515,893 issued May 7, 1985); anti-CD25 or anti-Tac antibodies such as CHI-621 (SIMULECT®) and ZENAPAX® (See U.S. Pat. No. 5,693,762 issued Dec. 2, 1997); anti-CD4 antibodies such as the cM-7412 antibody (Choy et al. *Arthritis Rheum* 39(1):52-56 (1996)); anti-CD52 antibodies such as CAMPATH-1H (Riechmann et al. *Nature* 332:323-337 (1988)); anti-Fc receptor antibodies such as the M22 antibody directed against FcγRI as in Graziano et al. *J. Immunol.* 155 (10):4996-5002 (1995); anti-carcinoembryonic antigen (CEA) antibodies such as hMN-1 4 (Sharkey et al. *Cancer Res.* 55(23Suppl): 5935s-5945s (1995); antibodies directed against breast epithelial cells including huBrE-3, hu-Mc 3 and CHL6 (Ceriani et al. *Cancer Res.* 55(23): 5852s-5856s (1995); and Richman et al. *Cancer Res.* 55(23 Supp): 5916s-5920s (1995)); antibodies that bind to colon carcinoma cells such as C242 (Litton et al. *Eur J Immunol.* 26(1): 1-9 (1996)); anti-CD38 antibodies, e.g. AT 13/5 (Ellis et al. *J. Immunol.* 155(2):925-937 (1995)); anti-CD33 antibodies such as Hu M195 (Jurcic et al. *Cancer Res* 55(23 Suppl):5908s-5910s (1995) and CMA-676 or CDP771; anti-CD22 antibodies such as LL2 or LymphoCide (Juweid et al. *Cancer Res* 55(23 Suppl):5899s-5907s (1995)); anti-EpCAM antibodies such as 17-1A (PANOREX®); anti-GpIIb/IIIa antibodies such as abciximab or c7E3 Fab (REOPRO®); anti-RSV antibodies such as MEDI-493 (SYNAGIS®); anti-CMV antibodies such as PROTOVIR®; anti-HIV antibodies such as PRO542; anti-hepatitis antibodies such as the anti-Hep B antibody OSTAVIR®; anti-CA 125 antibodies, such as OvaRex; anti-idiotypic GD3 epitope antibody BEC2; anti-αvβ3 antibodies, including VITAXIN®; anti-human renal cell carcinoma antibody such as ch-G250; ING-1; anti-human 17-1A antibody (3622W94); anti-human colorectal tumor antibody (A33); anti-human melanoma antibody R24 directed against GD3 ganglioside; anti-human squamous-cell carcinoma (SF-25); and anti-human leukocyte antigen (HLA) antibodies such as Smart ID10 and the anti-HLA DR antibody Oncolym (Lym-1). The preferred target antigens for the antibody herein are: HER2 receptor, VEGF, IgE, CD20, CD11a, and CD40.

Aside from the antibodies specifically identified above, the skilled practitioner could generate antibodies directed against an antigen of interest, e.g., using the techniques described below.

(i) Antigen Selection and Preparation

The antibody herein is directed against an antigen of interest. Preferably, the antigen is a biologically important polypeptide and administration of the antibody to a mammal suffering from a disease or disorder can result in a therapeutic benefit in that mammal. However, antibodies directed against nonpolypeptide antigens (such as tumor-associated glycolipid antigens; see U.S. Pat. No. 5,091,178) are also contemplated. Where the antigen is a polypeptide, it may be a transmembrane molecule (e.g. receptor) or ligand such as a growth factor. Exemplary antigens include those proteins described in section (3) below. Exemplary molecular targets for antibodies encompassed by the present invention include CD proteins such as CD3, CD4, CD8, CD19, CD20, CD22 and CD34; members of the ErbB receptor family such as the EGFR, HER2, HER3 or HER4 receptor; cell adhesion molecules such as LFA-1, Mac1, p150,95, VLA-4, ICAM-1, VCAM and αv/β3 integrin including either α or β subunits thereof (e.g. anti-CD11a, anti-CD18 or anti-CD11b antibodies); growth factors such as VEGF; IgE; blood group antigens; flk2/flt3 receptor; obesity (OB) receptor; mpl receptor; CTLA-4; protein C, or any of the other antigens mentioned herein.

Soluble antigens or fragments thereof, optionally conjugated to other molecules, can be used as immunogens for generating antibodies. For transmembrane molecules, such as receptors, fragments of these (e.g. the extracellular domain of a receptor) can be used as the immunogen. Alternatively, cells expressing the transmembrane molecule can be used as the immunogen. Such cells can be derived from a natural source (e.g. cancer cell lines) or may be cells which have been transformed by recombinant techniques to express the transmembrane molecule.

Other antigens and forms thereof useful for preparing antibodies will be apparent to those in the art.

(ii) Polyclonal Antibodies

Polyclonal antibodies are preferably raised in animals by multiple subcutaneous (sc) or intraperitoneal (ip) injections of the relevant antigen and an adjuvant. It may be useful to conjugate the antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals are immunized against the antigen, immunogenic conjugates, or derivatives by combining, e.g., 100 μg or 5 μg of the protein or conjugate (for rabbits or mice, respectively) with 3 volumes of Freund's complete adjuvant and injecting the solution intradermally at multiple sites. One month later the animals are boosted with 1/5 to 1/10 the original amount of antigen or conjugate in Freund's complete adjuvant by subcutaneous injection at multiple sites. Seven to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

(iii) Monoclonal Antibodies

Monoclonal antibodies may be made using the hybridoma method first described by Kohler et al., *Nature*, 256:495 (1975), or may be made by recombinant DNA methods (U.S. Pat. No. 4,816,567).

In the hybridoma method, a mouse or other appropriate host animal, such as a hamster or macaque monkey, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice*, pp. 59-103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, *J. Immunol.*, 133:3001 (1984); Brodeur et al, *Monoclonal Antibody Production Techniques and Applications*, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

After hybridoma cells are identified that produce antibodies of the desired specificity, affinity, and/or activity, the clones may be subcloned by limiting dilution procedures and grown by standard methods (Goding, *Monoclonal Antibodies: Principles and Practice*, pp. 59-103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography. Preferably the protein A affinity chromatography procedure described herein is used.

DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells.

The DNA also may be modified, for example, by substituting the coding sequence for human heavy- and light-chain constant domains in place of the homologous murine sequences (U.S. Pat. No. 4,816,567; Morrison, et al., *Proc. Natl Acad. Sci. USA,* 81:6851 (1984)), or by covalently joining to the immunoglobulin coding sequence all or part of the coding sequence for a non-immunoglobulin polypeptide.

Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

In a further embodiment, monoclonal antibodies can be isolated from antibody phage libraries generated using the techniques described in McCafferty et al., *Nature,* 348:552-554 (1990). Clackson et al., *Nature,* 352:624-628 (1991) and Marks et al., *J. Mol. Biol.,* 222:581-597 (1991) describe the isolation of murine and human antibodies, respectively, using phage libraries. Subsequent publications describe the production of high affinity (nM range) human antibodies by chain shuffling (Marks et al., *Bio/Technology,* 10:779-783 (1992)), as well as combinatorial infection and in vivo recombination as a strategy for constructing very large phage libraries (Waterhouse et al., *Nuc. Acids. Res.,* 21:2265-2266 (1993)). Thus, these techniques are viable alternatives to traditional hybridoma techniques for isolation of monoclonal antibodies.

(iv) Humanized and Human Antibodies

A humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., *Nature,* 321:522-525 (1986); Riechmann et al., *Nature,* 332:323-327 (1988); Verhoeyen et al., *Science,* 239:1534-1536 (1988)), by substituting rodent CDRs or CDR sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human FR for the humanized antibody (Sims et al., *J. Immunol.,* 151:2296 (1993)). Another method uses a particular framework derived from the consensus sequence of all human antibodies of a particular subgroup of light or heavy chains. The same framework may be used for several different humanized antibodies (Carter et al., *Proc. Natl. Acad. Sci. USA,* 89:4285 (1992); Presta et al., *J. Immnol.,* 151:2623 (1993)).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the CDR residues are directly and most substantially involved in influencing antigen binding.

Alternatively, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci. USA,* 90:2551 (1993); Jakobovits et al., *Nature,* 362:255-258 (1993); Bruggermann et al., *Year in Immuno.,* 7:33 (1993); and Duchosal et al. *Nature* 355:258 (1992). Human antibodies can also be derived from phage-display libraries (Hoogenboom et al., *J. Mol. Biol.,* 227:381 (1991); Marks et al., *J. Mol. Biol.,* 222:581-597 (1991); Vaughan et al. *Nature Biotech* 14:309 (1996)).

(v) Antibody Fragments

Various techniques have been developed for the production of antibody fragments. Traditionally, these fragments were derived via proteolytic digestion of intact antibodies (see, e.g., Morimoto et al. *Journal of Biochemical and Biophysical Methods* 24:107-117 (1992) and Brennan et al., *Science,* 229:81 (1985)). However, these fragments can now be produced directly by recombinant host cells. For example, the antibody fragments can be isolated from the antibody phage libraries discussed above. Alternatively, Fab'-SH fragments can be directly recovered from *E. coli* and chemically coupled to form F(ab')$_2$ fragments (Carter et al., *Bio/Technology* 10:163-167 (1992)). According to another approach, F(ab')$_2$ fragments can be isolated directly from recombinant host cell culture. Other techniques for the production of antibody fragments will be apparent to the skilled practitioner. In other embodiments, the antibody of choice is a single chain Fv fragment (scFv). See WO 93/16185.

(vi) Multispecific Antibodies

Multispecific antibodies have binding specificities for at least two different antigens. While such molecules normally will only bind two antigens (i.e. bispecific antibodies, BsAbs), antibodies with additional specificities such as trispecific antibodies are encompassed by this expression when used herein.

Methods for making bispecific antibodies are known in the art. Traditional production of full length bispecific antibodies is based on the coexpression of two immunoglobulin heavy chain-light chain pairs, where the two chains have different specificities (Millstein et al., *Nature,* 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., *EMBO J.,* 10:3655-3659 (1991).

According to another approach described in WO96/27011, the interface between a pair of antibody molecules can be engineered to maximize the percentage of heterodimers which are recovered from recombinant cell culture. The preferred interface comprises at least a part of the $C_H3$ domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science,* 229: 81 (1985) describe a procedure wherein intact antibodies are proteolytically cleaved to generate $F(ab')_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli,* which can be chemically coupled to form bispecific antibodies. Shalaby et al., *J. Exp. Med.,* 175: 217-225 (1992) describe the production of a fully humanized bispecific antibody $F(ab')_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., *J. Immunol.,* 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA,* 90:6444-6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., *J. Immunol.,* 152:5368 (1994). Alternatively, the antibodies can be "linear antibodies" as described in Zapata et al. *Protein Eng.* 8(10):1057-1062 (1995). Briefly, these antibodies comprise a pair of tandem Fd segments ($V_H$-$C_H1$-$V_H$-$C_H1$) which form a pair of antigen binding regions. Linear antibodies can be bispecific or monospecific.

Antibodies with more than two valencies are contemplated. For example, trispecific antibodies can be prepared. Tutt et al. *J. Immunol* 147: 60 (1991).

2. Immunoadhesins

The simplest and most straightforward immunoadhesin design combines the binding domain(s) of the adhesin (e.g. the extracellular domain (ECD) of a receptor) with the hinge and Fc regions of an immunoglobulin heavy chain. Ordinarily, when preparing the immunoadhesins of the present invention, nucleic acid encoding the binding domain of the adhesin will be fused C-terminally to nucleic acid encoding the N-terminus of an immunoglobulin constant domain sequence, however N-terminal fusions are also possible.

Typically, in such fusions the encoded chimeric polypeptide will retain at least functionally active hinge, $C_H2$ and $C_H3$ domains of the constant region of an immunoglobulin heavy chain. Fusions are also made to the C-terminus of the Fc portion of a constant domain, or immediately N-terminal to the $C_H1$ of the heavy chain or the corresponding region of the light chain. The precise site at which the fusion is made is not critical; particular sites are well known and may be selected in order to optimize the biological activity, secretion, or binding characteristics of the immunoadhesin.

In a preferred embodiment, the adhesin sequence is fused to the N-terminus of the Fc domain of immunoglobulin $G_1$ (Ig$G_1$). It is possible to fuse the entire heavy chain constant region to the adhesin sequence. However, more preferably, a sequence beginning in the hinge region just upstream of the papain cleavage site which defines IgG Fc chemically (i.e. residue 216, taking the first residue of heavy chain constant region to be 114), or analogous sites of other immunoglobulins is used in the fusion. In a particularly preferred embodiment, the adhesin amino acid sequence is fused to (a) the hinge region and $C_H2$ and $C_H3$ or (b) the $C_H1$, hinge, $C_H2$ and $C_H3$ domains, of an IgG heavy chain.

For bispecific immunoadhesins, the immunoadhesins are assembled as multimers, and particularly as heterodimers or heterotetramers. Generally, these assembled immunoglobulins will have known unit structures. A basic four chain structural unit is the form in which IgG, IgD, and IgE exist. A four chain unit is repeated in the higher molecular weight immunoglobulins; IgM generally exists as a pentamer of four basic units held together by disulfide bonds. IgA globulin, and occasionally IgG globulin, may also exist in multimeric form in serum. In the case of multimer, each of the four units may be the same or different.

Various exemplary assembled immunoadhesins within the scope herein are schematically diagramed below:

(a) $AC_L$-$AC_L$;
(b) $AC_H$-($AC_H$, $AC_L$-$AC_H$, $AC_L$-$V_HC_H$, or $V_LC_L$-$AC_H$);
(c) $AC_L$-$AC_H$-($AC_L$-$AC_H$, $AC_L$-$V_HC_H$, $V_LC_L$-$AC_H$, or $V_LC_L$-$V_HC_H$)
(d) $AC_L$-$V_HC_H$-($AC_H$, or $AC_L$-$V_HC_H$, or $V_LC_L$-$AC_H$);
(e) $V_LC_L$-$AC_H$-($AC_L$-$V_HC_H$, or $V_LC_L$-$AC_H$); and
(f) $(A-Y)_n$-$(V_LC_L$-$V_HC_H)_2$, wherein each A represents identical or different adhesin amino acid sequences;

$V_L$ is an immunoglobulin light chain variable domain;
$V_H$ is an immunoglobulin heavy chain variable domain;
$C_L$ is an immunoglobulin light chain constant domain;
$C_H$ is an immunoglobulin heavy chain constant domain;
n is an integer greater than 1;
Y designates the residue of a covalent cross-linking agent.

In the interests of brevity, the foregoing structures only show key features; they do not indicate joining (J) or other domains of the immunoglobulins, nor are disulfide bonds shown. However, where such domains are required for binding activity, they shall be constructed to be present in the ordinary locations which they occupy in the immunoglobulin molecules.

Alternatively, the adhesin sequences can be inserted between immunoglobulin heavy chain and light chain sequences, such that an immunoglobulin comprising a chimeric heavy chain is obtained. In this embodiment, the adhesin sequences are fused to the 3' end of an immunoglobulin heavy chain in each arm of an immunoglobulin, either between the hinge and the $C_H2$ domain, or between the $C_H2$ and $C_H3$ domains. Similar constructs have been reported by Hoogenboom, et al., *Mol. Immunol.* 28:1027-1037 (1991).

Although the presence of an immunoglobulin light chain is not required in the immunoadhesins of the present invention, an immunoglobulin light chain might be present either covalently associated to an adhesin-immunoglobulin heavy chain fusion polypeptide, or directly fused to the adhesin. In the former case, DNA encoding an immunoglobulin light chain is typically coexpressed with the DNA encoding the adhesin-immunoglobulin heavy chain fusion protein. Upon secretion, the hybrid heavy chain and the light chain will be covalently associated to provide an immunoglobulin-like structure comprising two disulfide-linked immunoglobulin heavy chain-light chain pairs. Methods suitable for the preparation of such structures are, for example, disclosed in U.S. Pat. No. 4,816,567, issued 28 Mar. 1989.

Immunoadhesins are most conveniently constructed by fusing the cDNA sequence encoding the adhesin portion in-frame to an immunoglobulin cDNA sequence. However, fusion to genomic immunoglobulin fragments can also be used (see, e.g. Aruffo et al., *Cell* 61:1303-1313 (1990); and Stamenkovic et al., *Cell* 66:1133-1144 (1991)). The latter type of fusion requires the presence of Ig regulatory sequences for expression. cDNAs encoding IgG heavy-chain constant regions can be isolated based on published sequences from cDNA libraries derived from spleen or peripheral blood lymphocytes, by hybridization or by polymerase chain reaction (PCR) techniques. The cDNAs encoding the "adhesin" and the immunoglobulin parts of the immunoadhesin are inserted in tandem into a plasmid vector that directs efficient expression in the chosen host cells.

3. Other $C_H2/C_H3$ Region-containing Proteins

In other embodiments, the protein to be purified is one which is fused to, or conjugated with, a $C_H2/C_H3$ region. Such fusion proteins may be produced so as to increase the serum half-life of the protein and/or to facilitate purification of the protein by protein A affinity chromatography. Examples of biologically important proteins which can be conjugated this way include renin; a growth hormone, including human growth hormone and bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor VIIIC, factor IX, tissue factor, and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin such as human serum albumin; Muellerian-inhibiting substance; relaxin A-chain; relaxin B-chain; prorelaxin; mouse gonadotropin-associated peptide; a microbial protein, such as beta-lactamase; DNase; IgE; a cytotoxic T-lymphocyte associated antigen (CTLA), such as CTLA-4; inhibin; activin; vascular endothelial growth factor (VEGF); receptors for hormones or growth factors; Protein A or D; rheumatoid factors; a neurotrophic factor such as bone-derived neurotrophic factor (BDNF), neurotrophin-3, -4, -5, or -6 (NT-3, NT-4, NT-5, or NT-6), or a ner growth factor such as NGF-β; platelet-derived growth factor (PDGF); fibroblast growth factor such as aFGF and bFGF; epidermal growth factor (EGF); transforming growth factor (TGF) such as TGF-alpha and TGF-beta, including TGF-β1, TGF-β2, TGF-β3, TGF-β4, or TGF-β5; insulin-like growth factor-I and -II (IGF-I and IGF-II); des(1-3)-IGF-I (brain IGF-I), insulin-like growth factor binding proteins; CD proteins such as CD3, CD4, CD8, CD19 and CD20; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the AIDS envelope; transport proteins; homing receptors; addressins; regulatory proteins; integrins such as CD11a, CD11b, CD11c, CD18, an ICAM, VLA-4 and VCAM; a tumor associated antigen such as EGFR, HER2, HER3 or HER4 receptor; and fragments of any of the above-listed polypeptides.

4. Protein A Affinity Chromatography

The protein to be purified using the method described herein is generally produced using recombinant techniques or isolated from a native source thereof. Methods for producing recombinant proteins are described, e.g., in U.S. Pat. Nos. 5,534,615 and 4,816,567, specifically incorporated herein by reference.

Preferably the $C_H2/C_H3$ region-containing protein or product of interest is an antibody, e.g. one which binds an antigen selected from the group consisting of HER2, vascular endothelial growth factor (VEGF), IgE, CD20, CD40, CD11a, tissue factor (TF), prostate stem cell antigen (PSCA), interleukin-8 (IL-8), epidermal growth factor receptor (EGFR), HER3, HER4, α4β7 or α5β3. For instance, the antibody may bind the HER2 antigen as leaching of protein A during protein A affinity chromatography of such antibodies, was found to be particularly problematic. More specific examples of antibodies herein include Trastuzumab, humanized 2C4, humanized CD11a antibody, or humanized VEGF antibody. Other $C_H2/C_H3$ region-containing proteins of particular interest herein are immunoadhesins, e.g. TNF receptor immunoadhesin (e.g. etanercept, ENBREL®.

When using recombinant techniques, the protein may be produced intracellularly, in the periplasmic space, or directly secreted into the medium. If the protein is produced intracellularly, as a first step, the particulate debris, either host cells or lysed fragments, is removed, for example, by centrifugation or ultrafiltration. Where the protein is secreted into the medium, the recombinant host cells may also be separated from the cell culture medium by centrifugation or tangential flow filtration, for example.

The method herein reduces leaching of protein A which may occur during protein A affinity chromatography of a composition comprising a $C_H2/C_H3$ region-containing protein and one or more impurities.

In one embodiment, the susceptibility of the protein to be associated with protein A leaching during protein A affinity chromatography is first assessed. Thus, the protein is subjected to protein A affinity chromatography and protein A leaching in the recovered composition is determined. For instance, where the recovered composition comprises greater than about 20 ng protein A per mg protein of interest (ng/mg), e.g. from about 20 ng/mg to about 500 ng/mg protein A, this may be considered unacceptable levels of leached protein A, in which case subsequent protein A chromatographic purification of the protein will include step(s) which reduce the amount of protein A in the recovered composition. Preferably, the amount of protein A in the recovered protein composition following the implementation of these step(s) is in the range from about 0 ng protein A per mg protein of interest (ng/mg) to about 15 ng/mg.

Protein A leaching can be measured using various techniques including enzyme linked immunosorbent assay (ELISA), SDS PAGE, Western blot, high pressure liquid chromatography (HPLC), mass spectrometry, etc.

The preferred assay for measuring leached protein A is ELISA. For example, a sandwich ELISA may be used. In this assay format, anti-protein A antibody may be coated onto a 96 well microtiter plate. Samples may be diluted to 0.2 mg/mL product antibody and applied onto the wells. The protein A in the samples binds to the coat antibody and the amount of bound protein A can be detected with anti-protein A coupled to Horseradish Peroxidase (HRP). To prevent product antibody inhibiting binding of protein A to the coat antibody and the HRP-conjugated antibody, one may match the inhibition exerted by product antibody in diluted samples using individual protein A standard curves that are spiked with 0.2 mg/mL homologous product antibody. Although this method is more time-consuming and costly, it provides a more accurate and precise determination of protein A levels. An exemplary protein A sandwich ELISA is described in more detail in the Example below.

Preferably, the method comprises reducing the temperature of the composition subjected to the protein A affinity chromatography, e.g. where the temperature of the composition is reduced below room temperature, for instance in the range from about 3° C. to about 20° C., e.g. from about 10° C. to about 18° C. The temperature of the composition may be reduced prior to and/or during protein A affinity chromatography thereof. However, according to the preferred embodiment of the invention, the method comprises lowering the temperature of the composition prior to subjecting the composition to protein A affinity chromatography, e.g. by lowering the temperature of harvested cell culture fluid (HCCF) which is subjected to chromatography.

In one embodiment, temperature reduction as disclosed above is combined with one or more other methods for reducing protein A leaching, e.g. by adding protease inhibitor(s) and/or lowering the pH of the composition that is subjected to protein A affinity chromatography.

Protease inhibitors (such as phenylmethylsulfonyl fluoride (PMSF), 4-(2-aminoethyl)-benzenesulfonyl-fluoride, hydrochloride (AEBSF) (PEFABLOC® SC), pepstatin, benzamidine, and/or a metal ion chelator such as EDTA or imidazole for inhibiting metalloprotease activity) may be added to the composition that is subjected to protein A affinity chromatography. The preferred protease inhibitors inhibit metalloprotease activity (e.g. EDTA) and/or inhibit certain serine protease activities. For instance, one may add the protease inhibitor(s) to the composition subjected to protein A affinity chromatography in an amount from about 0.001 µM to about 100 mM. The protease inhibitor(s) may be added to the composition before and/or during protein A affinity chromatography.

The present invention also contemplates lowering the pH of the composition prior to subjecting it to protein A affinity chromatography, e.g. to a pH in the range from about 2.5 to about 3.5, in order to reduce protein A leaching.

Various exemplary equilibration, loading, washing, and elution buffers and methods will now be described.

As an optional preliminary step, the solid phase for the protein A affinity chromatography may be equilibrated with a suitable buffer before chromatography of the protein of interest. For example, the equilibration buffer may be 25 mM Tris, 25 mM NaCl, 5 mM EDTA, pH 7.1.

The preparation comprising the protein of interest may then be loaded on the equilibrated solid phase using a loading buffer which may be the same as the equilibration buffer. As the contaminated preparation flows through the solid phase, the protein is adsorbed to the immobilized protein A.

Sometimes, certain impurities (such as Chinese Hamster Ovary Proteins, CHOP, where the protein is produced in a CHO cell) may bind nonspecifically to the solid phase, protein or protein A. If this occurs, an "intermediate wash step" may be used to remove such impurities prior to elution of the protein of interest. The solid phase may be equilibrated with equilibration buffer before beginning the intermediate wash step.

In one embodiment, the intermediate wash step is performed using a hydrophobic electrolyte solvent, e.g. where the hydrophobic electrolyte in the wash solvent is TMAC and/or TEAC. See U.S. Pat. Nos. 6,127,526 and 6,333,398 (Blank, G.). While a single hydrophobic electrolyte may be present in the wash solvent, in certain embodiments, two or more such electrolytes may be used. The hydrophobic electrolyte is preferably added to a pH buffered solution having a pH in the range from about 4 to about 8, and preferably in the range from about 5 to about 7. Suitable buffers for this purpose include Tris, phosphate, MES, and MOPSO buffers. The preferred final concentration for the hydrophobic electrolyte in the wash solvent is in the range from about 0.1 to about 1.0 M, and preferably in the range from about 0.25 to about 0.5M.

In an alternative embodiment, the intermediate wash buffer may comprise salt and a further compound, where the further compound is (a) detergent (preferably polysorbate, e.g. polysorbate 20 or polysorbate 80); (b) solvent (preferably hexylene glycol); and (c) polymer (preferably PEG).

The salt employed may be selected based on the protein of interest, but preferably is acetate (e.g. sodium acetate), especially where the antibody is an anti-HER2 antibody such as Trastuzumab; or citrate (e.g. sodium citrate), particularly where the antibody is an anti-IgE antibody such as E26.

The amounts of the salt and further compound in the composition are such that the combined amount elutes the impurity or impurities, without substantially removing the protein of interest. Preferred salt concentrations in such wash buffers are from about 0.1 to about 2M, and more preferably from about 0.2M to about 0.6M. Useful detergent concentrations are from about 0.01 to about 5%, more preferably from about 0.1 to 1%, and most preferably about 0.5%, e.g. where the detergent is polysorbate. Exemplary solvent concentrations are from about 1% to 40%, preferably from about 5 to about 25%. The preferred concentration of the solvent (hexylene glycol) for E26 is about 20%, whereas for Trastuzumab the preferred concentration of the solvent (again hexylene glycol) is about 10%. Where the further compound is a polymer (e.g. PEG 400 or PEG 8000), the concentration thereof may, for example, be from about 1% to about 20%, preferably from about 5% to about 15%.

In another embodiment, the intermediate wash step involves the use of a highly concentrated buffer solution, e.g. a buffer at a concentration of greater than about 0.8M, e.g. up to about 2M, and preferably in the range from about 0.8M to about 1.5M, most preferably about 1M. In this embodiment, the buffer is preferably a Tris buffer, such as Tris acetate.

The pH of the intermediate wash buffer is preferably from about 4 to about 8, more preferably from about 4.5 to about 5.5, and most preferably about 5.0. In another preferred embodiment, the pH is about 7.0.

The protein of interest may be recovered from the column, using a suitable elution buffer. The protein may, for example, be eluted from the column using an elution buffer having a low pH, e.g. in the range from about 2 to about 5, and preferably in the range from about 2.5 to about 3.5. Examples of elution buffers for this purpose include citrate or acetate buffers. The eluted protein preparation may be subjected to additional purification steps either prior to, or after, the protein A affinity chromatography step. Exemplary further purification steps include, but are not limited to, filtration, hydroxylapatite chromatography; dialysis; affinity chromatography using an antibody to capture the protein; hydrophobic interaction chromatography (HIC); ammonium sulphate precipitation; anion or cation exchange chromatography; ethanol precipitation; reverse phase HPLC; chromatography on silica; chromatofocusing; gel filtration, etc.

The protein thus recovered may be formulated in a pharmaceutically acceptable carrier and is used for various diagnostic, therapeutic or other uses known for such molecules.

The following examples are offered by way of illustration and not by way of limitation. The disclosures of all citations in the specification are expressly incorporated herein by reference.

EXAMPLE 1

Temperature Reduction for Reducing Protein A Leaching During Protein A Affinity Chromatography Protein A affinity chromatography is a powerful and widely-used tool for purifying antibodies. It efficiently removes host cell proteins, DNA, and small molecules from the product. Harvested cell culture fluid (HCCF) can be loaded directly onto the resin and the antibody binds to the protein A. Low pH elutes the bound antibody, but may carry leached protein A into the product pool. Since protein A ligand is immunogenic, derived from *Staphylococcus aureus*, it must be cleared from the product pool by downstream processing.

To characterize the temperature dependence of protein A leaching, the effect of temperature on protein A leaching was evaluated with respect to the following proteins:
1. Recombinant humanized HER2 antibody Trastuzumab (HERCEPTIN®); Carter et al., *Proc. Natl. Acad. Sci. USA*, 89:4285-4289 (1992), U.S. Pat. No. 5,725,856, U.S. Pat No. 5,821,337, and FIGS. 4A-B herein.
2. Humanized CD11a antibody MHM24, RAPTIVA™; Werther et al. *J. Immunology* 157: 4986-4995 (1996), U.S. Pat. No. 5,622,700, WO 98/23761, and FIGS. 6A-B herein.
3. Humanized VEGF antibody A4.6.1, F(ab)-12, AVASTIN®; Kim et al., *Growth Factors*, 7:53-64 (1992), Presta et al *Cancer Research* 57: 4593-4599 (1997), International Publication No. WO 96/30046, WO 98/45331, published Oct. 15, 1998, and FIGS. 7A-B herein.
4. Humanized 2C4; WO01/00245, and FIGS. 5A-B herein.

Materials and Methods

Small-Scale: All small-scale experiments were performed using an AKTA EXPLORER 100™. The temperature was controlled by immersing the column and the 5 ml stainless-steel upstream line in a water bath. controlled to the desired temperature of the run. The inlet line acted as a heat exchanger cooling or heating the HCCF prior to entering the protein A column, similar to the effect of chilling the HCCF in a tank at manufacturing scale. The outlet temperature was measured to be sure the desired temperature was achieved.

Several sets of protein A runs were performed to determine the temperature dependence of protein A leaching from PROSEP A™ and PROSEP vA™ for various antibodies. Various lots of each type of resin were tested. Each condition was tested in triplicate. The column was pre-cycled with 3 column volumes (CV's) of elution buffer and 3 CV's of regeneration buffer prior to each use, and stored in 0.1 M sodium acetate, 2% benzyl alcohol pH 5.0 after each use. Trastuzumab was run at 7 temperature settings (10, 12, 15, 18, 20, 25, and 30° C.). The other antibodies were run at 3 temperature settings (10, 20, and 30° C.). The temperatures were run out of order to reduce systematic error. Trastuzumab HCCF from six 400L runs were compared. Using one lot of Trastuzumab HCCF on one lot of resin at 20° C., the effect of bed height on protein A leaching was explored.

Pilot Scale: The pilot scale experiments were run with Trastuzumab HCCF. The HCCF was stored and chilled in a 400L-jacketed tank. The temperature of the HCCF was controlled to within 1° C. of the desired temperature. The temperature was measured in the tank, after the pump but prior to the column, and at the outlet of the column. The column was pre-cycled with 3 CV's elution buffer and 3 CV's of regeneration buffer prior to each use, and stored in 0.1 M sodium acetate, 2% benzyl alcohol pH 5.0 after each use. Trastuzumab was run at 7 temperature settings (10, 12, 15, 18, 20, 25, and 30° C.). The temperatures were run out of order to reduce systematic error.

Full Scale (12,000 L cell culture): The column was 80 cm in diameter by 20 cm high for a total volume of 100.5 L PROSEP vA™. Five harvests were recovered through the protein A step. The HCCF was collected and held at 15+/−3° C. for the duration of loading.

Analysis: Each protein A pool was analyzed by OD at A280-A320/extinction coefficient for concentration. The extinction coefficients were 1.5 (mg/ml)-1 cm-1 for Trastuzumab and humanized 2C4, 1.46 (mg/ml)-1 cm-1 for humanized CD11a antibody, 1.7 (mg/ml)-1 cm-1 for humanized VEGF antibody. The yield of each run was calculated. If the yield was less than 85%, the run was repeated. Protein A leaching in each pool was measured using ELISA. Each sample was assayed in triplicate on separate plates to encompass as much of the assay and dilution variability as possible.

ELISA: Chicken anti-protein A is coated on a 96-well, polystyrene, microtiter plate and incubated at 2-8° C. for 12-72 hours. The plate is washed with a PBS/TWEEN 20™ Wash Buffer and Assay Diluent containing NaCl/NaPO4/Fish Gelatin/TWEEN 20™ is added to the plate wells to block any unbound coat antibody. The plate is incubated at room temperature for 1-2 hours. During the plate incubation, protein A standard curve is prepared at a range of 0.39-50 ng/ml using Assay Diluent spiked with 0.2 mg/ml of product antibody homologous to the product antibody contained in the samples. Samples are diluted with unspiked Assay Diluent to 0.2 mg/ml of product antibody. An assay control prepared from the same product antibody is used. After the 1-2 hour incubation, the plate is washed with Wash Buffer to remove the Assay Diluent. The standard curve, assay control and samples are then applied onto the plate wells, and incubated at room temperature for 2 hours where the protein A in the standards, control and samples will bind to the coat antibody. After the 2 hour incubation, the plate is then washed with Wash Buffer to remove any unbound antibodies as well as the sample matrix. HRP-conjugated Chicken anti-protein A is then applied onto the wells and incubated at room temperature for 1 hour. The HRP-conjugated Chicken anti-protein A will bind to any bound protein A. After the 1 hour incubation, the plate is washed again with Wash Buffer to remove any unbound antibodies. The substrate solution, consisting of o-phenylenediamine tablet dissolved in $H_2O_2$ in phosphate buffered saline (PBS), is then added onto the plate wells and is processed by the HRP enzyme, causing the substrate solution to change color. Once the substrate color has reached a desired OD range, the enzyme reaction is stopped by the addition of sulfuric acid. The amount of bound protein A is determined by measuring the Optical Density at 490 nm using a microtiter plate reader.

Results and Discussion

Several antibodies were purified from HCCF by protein A affinity chromatography on PROSEP A™ or PROSEP vA™ at up to 7 temperatures at small scale to characterize the effect of temperature on protein A leaching. Protein A leaching is affected by temperature to varying degrees for the antibodies tested (FIG. 1). Protein A leaching during elution of HER2 antibodies, Trastuzumab and humanized 2C4, is most significantly affected, while humanized VEGF and humanized CD11a antibodies were only slightly affected by temperature. The small error bars in conjunction with randomized run order ensure the effect of temperature on protein A leaching is real. The trend-lines on the graph represent an exponential fit for each set of data. This type of non-linear correlation would be consistent with temperature-activated proteolytic cleavage.

Several lots of Trastuzmab HCCF from 400L pilot plant runs were run on PROSEP A™ at room temperature, to investigate the effect of HCCF lot-to-lot variability on Protein A leaching The results are shown in Table 1 below. Each lot of HCCF was run on PROSEP A™ in triplicate. The lots showed a range of protein A leaching from 4 to 13 ng/mg with a small standard deviation of 0.2 to 1.1 ng/mg. These numbers are low in comparison to previous protein A ELISA results using Trastuzumab. The positive control run in the ELISA on that day also ran low. Compared only with each other and not with samples assayed at other times, the results show some variability in leaching between lots of Trastuzumab HCCF.

TABLE 1

Lot-to-Lot Variability
Runs were performed in triplicate on PROSEP A ™ resin packed in a 0.66 cm diameter by 20 cm high column. The column was equilibrated and washed with 25 mM Tris, 25 mM NaCl, 5 mM EDTA, pH 7.1, washed with 25 mM Tris, 25 mM NaCl, 0.5 M TMAC, 5 mM EDTA pH 5.0, eluted with 25 mM citrate pH 2.8, regenerated with 0.1 M phosphoric acid, and stored in 0.2 M sodium acetate, 2% benzyl alcohol pH 5.0 at 40 CV/hr. Trastuzumab from the 400 L pilot plant runs was run on a bed height of 20 cm, loaded to 20 g Trastuzumab/L resin, eluted with 25 mM citrate pH 2.8, and pooled from 0.1 AU to 2 CV's.

| Lot of Trastuzumab HCCF | Protein A (ng/mg) |
|---|---|
| 1 | 7 +/− 0.3 |
| 2 | 4 +/− 0.4 |
| 3 | 5 +/− 0.2 |
| 4 | 7 +/− 0.8 |
| 5 | 13 +/− 1.1 |
| 6 | 7 +/− 0.7 |

FIG. 2 compares the effect of temperature on protein A leaching between PROSEP A™ and PROSEP vA™ for 3 antibodies. For humanized CD11a antibody, the PROSEP A™ and PROSEP vA™ results overlay exactly. In the cases of humanized 2C4 and Trastuzumab, the results do not overlay, but they are within the expected range for lot-to-lot variability of the resins (Table 1), and the results are probably not due to differences between PROSEP A™ and PROSEP vA™. The effect of temperature on protein A leaching from PROSEP A™ is equivalent to that from PROSEP vA™.

The product sequence of increasing leaching shown in FIG. 1 may have been related to inconsistencies in running each antibody, since we ran each at its pre-determined manufacturing conditions. Since the resin bed heights and elution buffers were not the same for each antibody tested initially, the possible dependence on bed height and elution buffer was also explored. Humanized 2C4 was tested previously using the acetate elution buffer, and the results are shown in Table 2. Humanized 2C4 was run at lab scale at room temperature and at pilot scale at 15° C. Within the variability between the runs and error in the assay, all the conditions produced similar leached protein A results. Citrate and acetate have approximately equivalent effects on protein A leaching. Bed height was the other potential contributor to the higher levels of protein A leaching seen with humanized 2C4 and Trastuzumab in comparison with the other antibodies tested. When one lot of Trastuzumab HCCF was run on three bed heights in triplicate, the leached protein A results were nearly identical as shown in Table 2. Bed height does not appear to affect the level of protein A leaching.

TABLE 2

Effect of Bed Height on Protein A Leaching
Runs were performed at 20° C. using Trastuzumab HCCF on
PROSEP vA ™ resin packed in a 0.66 cm diameter by 20 cm
high column. The column was equilibrated and washed with 25 mM
Tris, 25 mM NaCl, 5 mM EDTA, pH 7.1, washed with 25 mM Tris,
25 mM NaCl, 0.5 M TMAC, 5 mM EDTA pH 5.0 or 7.1, eluted with
either 25 mM citrate pH 2.8, or 0.1 M acetic acid pH 2.9, regenerated
with 0.1 M phosphoric acid, and stored in 0.2 M sodium acetate, 2%
benzyl alcohol pH 5.0 at 40 CV/hr. The titer of Trastuzumab pilot plant
400 L HCCF was 0.7 mg/ml, and the column was loaded to 20 g
Trastuzumab per liter of resin. The elution pool was collected from
0.2 AU to 2 CV's.

| Bed Height cm | Protein A ng/mg |
|---|---|
| 10 | 55 +/− 6 |
| 14 | 50 +/− 2 |
| 20 | 55 +/− 0 |

The effect of elution buffer on protein A leaching was also assessed. Citrate and acetate have approximately equivalent effects on protein A leaching as shown in Table 3 below.

TABLE 3

Effect of Elution Buffer on Leached Protein A
Leached protein A is shown in parts per million humanized 2C4 antibody
was run on a 20 cm bed height column, loaded to 14 g humanized
2C4 per liter resin antibody. The column was equilibrated and washed
with 25 mM Tris, 25 mM NaCl, 5 mM EDTA, pH 7.1, washed with
25 mM Tris, 25 mM NaCl, 0.5 M TMAC, 5 mM EDTA pH 7.1, eluted
with 0.1 M acetic acid pH 2.9, regenerated with 0.1 M phosphoric acid,
and stored in 0.2 M sodium acetate, 2% benzyl alcohol pH 5.0 at
40 CV/hr. Some runs were eluted with 25 mM citrate pH 2.8. The pool
was collected from 0.5 AU to 2 CV's pool volume. The lab scale runs
were performed on a 0.66 cm diameter column and the pilot scale runs
were performed using a 10 cm diameter column containing PROSEP A ™.
Two humanized 2C4 antibody runs were eluted with citrate and
three humanized 2C4 antibody runs were eluted with acetate at pilot
scale. Three humanized 2C4 antibody runs were performed with each
elution buffer at lab scale.

| MAb | Scale | Temperature ° C. | Protein A from Acetate (ng/mg) | Protein A from Citrate (ng/mg) |
|---|---|---|---|---|
| Humanized 2C4 | Lab | room temp. | 18 +/− 1 | 22 +/− 5 |
| Humanized 2C4 | Pilot | 15 | 10 +/− 2 | 15 +/− 6 |

Protein A leaching with respect to temperature for 2 lots of Trastuzumab HCCF at pilot scale (1.26 L column) is shown in FIG. 3. The same exponential trend at pilot scale observed at small scale was reproduced. Small-scale duplicate runs were performed using the lots of HCCF, which were used in the pilot plant. The pilot plant results line up exactly with lab scale results from runs performed with the same HCCF on the same lot of PROSEP vA™. Trastuzumab at full scale. The HCCF was chilled to 15+/−3° C. and run on PROSEP vA™ resin. Table 4 shows the level of protein A in the protein A pools for 5 runs. In all runs the leached protein A level was 10 ng/mg or less demonstrating that controlling the temperature of the HCCF controls protein A leaching.

TABLE 4

Leached Protein A In Protein A Pools 12,000 L Process
HCCF was chilled to 15 +/− 3° C. column was 100.5 L,
80 cm in diameter by 20 cm in height, and eluted with citrate.
Temperature was measured in the HCCF tank, between the
pump and the column, and at the outlet to the column. The column
was equilibrated and washed with 25 mM Tris, 25 mM NaCl, 5 mM
EDTA, pH 7.1, washed with 25 mM Tris, 25 mM NaCl, 0.5 M
TMAC, 5 mM EDTA pH 5.0, eluted with either 25 mM citrate
pH 2.8, regenerated with 0.1 M phosphoric acid, and stored in
0.2 M sodium acetate, 2% benzyl alcohol pH 5.0.

| Trastuzumab concentration (mg/mL) | Protein A in Pool (ng/mg) |
|---|---|
| 0.69 | 8 |
| 0.69 | 7 |
| 0.67 | 10 |
| 0.72 | 8 |
| 0.68 | 7 |

Conclusions

Temperature affects protein A leaching during protein A affinity chromatography of antibodies to varying degrees. Some antibodies are more affected than others; HER2 antibodies Trastuzumab and humanized 2C4 were greatly affected. The lower leaching antibodies are all run on 14 cm bed height columns and are eluted with 0.1 M acetic acid, while the higher-leaching ones are run on 20 cm bed height columns and eluted using 25 mM citric acid. The bed height correlation was investigated and found to have no influence on protein A leaching. Citrate or acetate elution had essentially equivalent effects on protein A leaching.

By controlling the HCCF temperature, the level of protein A in the protein A pool can be controlled, or reduced. A similar test was performed at pilot scale. Two lots of Trastuzumab HCCF were run on a 1.26L PROSEP vA™ column at 5 temperatures and the level of protein A in the elution pools was measured. Protein A leaching depended on temperature identically to the same HCCF run at small scale, and to other lots of HCCF run at small scale. At large scale, Trastuzumab HCCF was chilled to 15+/−3° C. and protein A leaching was controlled to less than or equal to 10 ng/mg. All antibodies are affected by temperature, but to varying degrees. At all scales, controlling the temperature of the HCCF during loading could control protein A leaching. Increasing HCCF temperature has an exponentially increasing effect on Protein A leaching.

EXAMPLE 2

Protease Inhibitors for Reducing Protein A Leaching
During Protein A Affinity Chromatography Protein A chromatography may be used as an initial capture step in a recovery process for an antibody, such as an antibody recombinantly produced by a Chinese Hamster Ovary (CHO) cell. This step achieves a high degree of purity while maintaining a high yield. Leaching of the Protein A ligand into the elution pool is a disadvantage of this step, which may require subsequent chromatography steps to remove the leached Protein A. PROSEP A™ and PROSEP vA™ resins which can be used for Protein A chromatography, comprise the Protein A ligand immobilized onto a controlled pore glass (CPG) backbone.

Protein A can leach from the CPG backbone through several mechanisms, including, but not limited to, mechanical shearing, low pH exposure during the elution phase, and/or proteolytic activity. As shown in Example 1 above, Protein A leaching was shown to be dependent on temperature during loading.

Protein A leaching was also shown to be partially inhibited by pH treatment of the harvested cell culture fluid (HCCF). In particular, a 2 hour incubation of HCCF at pH 3 reduced leaching from approximately 30 ppm to 4 ppm.

Proteases can be organized into four major classes based on their mode of action. These are serine, cysteine, metallo- and aspartic proteases. Inhibitors that selectively inhibit these classes were tested over a range of concentrations (Table 5). These inhibitors were individually added to Trastuzumab HCCF, and the conditioned HCCF was purified across PROSEP VA™ resin at a fixed temperature of 25° C. If a reduction in leached Protein A was observed with a specific inhibitor, its effect was re-examined at 15° C., a temperature known to reduce leaching. This allowed an examination of the combined effect of temperature and inhibitor concentration on Protein A leaching. The inhibitors listed in Table 5 below have been tested, with the exception of Pepstatin.

Results and Discussion

With increasing EDTA concentration, there was a decrease in Protein A leaching (FIG. 8). There was further a combined effect of EDTA and temperature on the inhibition of Protein A leaching.

With increasing PEFABLOC® concentration, there was a decrease in Protein A leaching (FIG. 9). This experiment shall be repeated at 15° C.

Aprotinin, another serine protease, did not have an effect on Protein A leaching (Table 6). Leupeptin, a protease inhibitor that can inhibit both serine and cysteine proteases, did not have an effect on Protein A leaching (Table 7).

TABLE 6

Effect of Aprotinin, a Serine Protease Inhibitor, on Protein A Leaching

| Aprotinin (mg) | Aprotinin (uM) | Protein A (ppm) | 1 Standard Deviation |
|---|---|---|---|
| 0 | 0 | 37.4 | 5.2 |
| 14 | 12 | 35.6 | 0.1 |
| 28 | 25 | 31.1 | 0.4 |
| 54 | 47 | 34.53 | 0.0 |

TABLE 7

Effect of Leupeptin, a Serine and Cysteine Protease Inhibitor, on Protein A Leaching

| Leupeptin (mM) | Protein A (ppm) | 1 Standard Deviation |
|---|---|---|
| 0 | 37.4 | 5.2 |
| 0.15 | 32.9 | 0.7 |
| 0.3 | 32.4 | 1.5 |
| 0.6 | 34.4 | 1.1 |

TABLE 5

Inhibitors of the Four Major Classes of Proteases

| Inhibitor | Class of Protease | Inhibits | Does not inhibit | Recommended Starting concentration |
|---|---|---|---|---|
| EDTA | Metallo- | thermolysin etc. | | N/A |
| PEFABLOC ® SC | Serine | trypsin, chymotrypsin, plasmin, plasma kallikrein, and thrombin. | | 0.4-4.0 mM |
| Aprotinin | Serine | plasmin, kallikrein, trypsin, and chymotrypsin | thrombin or Factor X | 0.01-0.3 mM |
| Leupeptin | Cysteine and serine with trypsin-like activity | trypsin, papain, plasmin, and cathepsin B. | | 1 mM |
| Pepstatin* | Aspartic | pepsin, renin, cathepsin D, chymosin, and many microbial acid proteases. | | 1 mM |

*Pepstatin is not soluble in aqueous solutions; a water soluble aspartic protease inhibitor may be used instead.

The invention claimed is:

1. A method of purifying a protein which comprises a $C_H2/C_H3$ region comprising:
    a. subjecting a composition comprising said protein to protein A affinity chromatography to provide a recovered composition and measuring leached protein A in said recovered composition; and
    b. if greater than about 20 ng protein A per mg of said protein is measured in said recovered composition, then performing subsequent purification of compositions comprising said protein by protein A affinity chromatography at a temperature in the range from about 3° C. to about 18° C., such that protein A leaching is reduced.

2. The method of claim 1 wherein the protein is an antibody.

3. The method of claim 2 wherein the antibody binds an antigen selected from the group consisting of HER2, vascular endothelial growth factor (VEGF), IgE, CD20, CD40, CD11a, tissue factor (TF), prostate stem cell antigen (PSCA), interleukin-8 (IL-8), epidermal growth factor receptor (EGFR), HER3, HER4, α4β7 and α5β3.

4. The method of claim 2 wherein the antibody is selected from the group consisting of Trastuzumab, humanized 2C4, humanized CD11a antibody, and humanized VEGF antibody.

5. The method of claim 2 wherein the antibody binds HER2 antigen.

6. The method of claim 5 wherein the antibody is Trastuzumab or humanized 2C4.

7. The method of claim 1 wherein the protein is an immunoadhesin.

8. The method of claim 7 wherein the immunoadhesin is a TNF receptor immunoadhesin.

9. The method of claim 1 further comprising exposing the composition subjected to protein A affinity chromatography to a protease inhibitor in order to reduce the protease activity.

10. The method of claim 9 wherein the protease inhibitor is EDTA or 4-(2-aminoethyl)-benzenesulfonyl-fluoride, hydrochloride (AEBSF).

11. The method of claim 1 further comprising adjusting the pH of the composition prior to protein A affinity chromatography to a pH in the range from about 2.5 to about 3.5.

12. A method of purifying a protein which comprises a $C_H2/C_H3$ region comprising:

a. subjecting a composition comprising said protein to protein A affinity chromatography to provide a recovered composition and measuring leached protein A in said recovered composition; and
b. if greater than about 20 ng protein A per mg of said protein is measured in said recovered composition, then performing subsequent purification of compositions comprising said protein by protein A affinity chromatography at a temperature in the range from about 10° C. to about 18° C., such that protein A leaching is reduced.